US009421183B2

(12) United States Patent
Cornblatt et al.

(10) Patent No.: US 9,421,183 B2
(45) Date of Patent: *Aug. 23, 2016

(54) COMPOSITIONS COMPRISING SULFORAPHANE OR A SULFORAPHANE PRECURSOR AND A MUSHROOM EXTRACT OR POWDER

(71) Applicant: Nutramax Laboratories, Inc., Edgewood, MD (US)

(72) Inventors: Brian Cornblatt, Westminster, MD (US); Grace Cornblatt, Westminster, MD (US); Anton Bzhelyansky, Baltimore, MD (US); Robert Henderson, Street, MD (US)

(73) Assignee: NUTRAMAX LABORATORIES, INC., Edgewood, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/586,765

(22) Filed: Dec. 30, 2014

(65) Prior Publication Data

US 2015/0110872 A1 Apr. 23, 2015

Related U.S. Application Data

(63) Continuation of application No. PCT/US2013/049248, filed on Jul. 3, 2013.

(60) Provisional application No. 61/668,328, filed on Jul. 5, 2012, provisional application No. 61/668,342, filed on Jul. 5, 2012, provisional application No. 61/668,386, filed on Jul. 5, 2012, provisional application No. 61/668,396, filed on Jul. 5, 2012, provisional application No. 61/668,364, filed on Jul. 5, 2012, provisional application No. 61/668,374, filed on Jul. 5, 2012, provisional application No. 61/794,417, filed on Mar. 15, 2013.

(51) Int. Cl.

| A61K 31/095 | (2006.01) |
| A61K 36/07 | (2006.01) |
| A61K 36/31 | (2006.01) |
| A61K 31/26 | (2006.01) |
| A61K 38/47 | (2006.01) |
| A61K 31/375 | (2006.01) |
| A61K 31/7028 | (2006.01) |
| A61K 33/06 | (2006.01) |
| A61K 45/06 | (2006.01) |
| A61K 9/00 | (2006.01) |
| A61K 9/28 | (2006.01) |
| A61K 31/194 | (2006.01) |
| A61K 47/42 | (2006.01) |
| A61K 31/19 | (2006.01) |
| A61K 36/28 | (2006.01) |
| A61K 31/716 | (2006.01) |
| A61K 36/06 | (2006.01) |
| A23L 1/30 | (2006.01) |
| A61K 31/357 | (2006.01) |

(52) U.S. Cl.
CPC .............. *A61K 31/26* (2013.01); *A23L 1/3002* (2013.01); *A61K 9/0053* (2013.01); *A61K 9/28* (2013.01); *A61K 31/19* (2013.01); *A61K 31/194* (2013.01); *A61K 31/357* (2013.01); *A61K 31/375* (2013.01); *A61K 31/7028* (2013.01); *A61K 31/716* (2013.01); *A61K 33/06* (2013.01); *A61K 36/06* (2013.01); *A61K 36/07* (2013.01); *A61K 36/28* (2013.01); *A61K 36/31* (2013.01); *A61K 38/47* (2013.01); *A61K 45/06* (2013.01); *A61K 47/42* (2013.01); *C12Y 302/01147* (2013.01); *A23V 2002/00* (2013.01)

(58) Field of Classification Search
None
See application file for complete search history.

(56) References Cited

U.S. PATENT DOCUMENTS

| 5,985,924 | A | 11/1999 | Ishikawa et al. |
| 2003/0091518 | A1* | 5/2003 | Pauly et al. ................. 424/59 |
| 2008/0311192 | A1 | 12/2008 | West et al. |
| 2010/0015109 | A1* | 1/2010 | Bias ............................ 424/93.44 |
| 2011/0020443 | A1 | 1/2011 | Liu et al. |
| 2013/0333075 | A1 | 12/2013 | Garcia Viguera et al. |

FOREIGN PATENT DOCUMENTS

| WO | WO 00/07607 A1 | 2/2000 |
| WO | WO2012/062947 A1 | 5/2012 |
| WO | 2012074412 A1 | 6/2012 |

OTHER PUBLICATIONS

Shapiro et al. Cancer Epidemiology, Biomarkers and Prevention, 7, p. 1091-1100, 1998.*
Shankar et al. Clin Cancer Res 14 (21), p. 6855-6866, 2008.*

(Continued)

*Primary Examiner* — Nissa Westerberg
(74) *Attorney, Agent, or Firm* — King & Schickli, PLLC

(57) ABSTRACT

The invention relates to the combination of a sulforaphane precursor, an enzyme capable of converting the sulforaphane precursor to sulforaphane, an enzyme potentiator, and a mushroom (preferably maitake, shiitake, or reishi mushroom) extract or powder. The invention also relates to the combination of sulforaphane or a derivative thereof and a mushroom (preferably maitake, shiitake, or reishi mushroom) extract or powder. The present invention also relates to the combination of a broccoli extract or powder and a mushroom (preferably maitake, shiitake, or reishi mushroom) extract or powder. The present provides compositions and methods relating to these combinations.

14 Claims, 6 Drawing Sheets

(56) References Cited

OTHER PUBLICATIONS

"China: Water Ban for Millions after Oil Spill Hits Refinery Town | Al Jazeera America." China: Water Ban for Millions after Oil Spill Hits Refinery Town | Al Jazeera America. Al Jazeera America, Apr. 12, 2014. 8 pages.

"Glutathione: Stepping into the Antioxidant Spotlight." Natural Products Insider 4.16 (2014). 13 pages.

"How Toxins Can Disrupt Hormones and Make You Fat." Functional Fitness Blog. Functional Fitness Blog, Feb. 5, 2012. 6 pages.

Ade, N., et al. "HMOX1 and NQO1 Genes Are Upregulated in Response to Contact Sensitizers in Dendritic Cells and THP-1 Cell Line: Role of the Keap1/Nrf2 Pathway." Toxicological Sciences 107.2 (2008): 451-60. 10 pages.

Agerbirk, Niels, Martin Vos, Jae Hak Kim, and Georg Jander. "Indole Glucosinolate Breakdown and Its Biological Effects." Phytochemistry Reviews 8.1 (2009): 101-20. 20 pages.

Agyeman, Abena, et al. "Transcriptomic and Proteomic Profiling of KEAP1 Disrupted and Sulforaphane-treated Human Breast Epithelial Cells Reveals Common Expression Profiles." Breast Cancer Research and Treatment 132.1 (2012): 175-87. 22 pages.

Ahn, Y.-H., et al. "Electrophilic Tuning of the Chemoprotective Natural Product Sulforaphane." Proceedings of the National Academy of Sciences 107.21 (2010): 9590-595. 6 pages.

Air Emissions from Oil and Gas Development in the Eagle Ford. 1 page.

Akramiene, Dalia, et al. "Effects of B-glucans on the Immune System." Medicina (Kaunas) 43.8 (2007): 597-606. 10 pages.

Aldini, Rita, et al. "Antiinflammatory Effect of Phytosterols in Experimental Murine Colitis Model: Prevention, Induction, Remission Study." PLoS ONE 9.9 (2014): E108112. 16 pages.

Allmyr, Mats. On the Fate of Triclosan in Humans. 2009. Department of Dental Medicine. Stockholm. 33 pages.

Almendarez, Sandy. "Vitamin K for Overall Care." Natural Products Insider14.11 (2009): 1-4. 4 pages.

Anne Bjørnebye, Vik. Www.nattopharma.com. May 2008. MenaQ7™, the natural vitamin K2 in foods—the next era. 2 pages.

Applegate, Evan. "Twenty-Five Years of Oil Spills." Bloomberg Business Week. Bloomberg, Mar. 13, 2014. 5 pages.

Ascherio, A., E. B. Rimm, M. A. Herman, E. L. Giovannucci, I. Kawachi, M. J. Stampfer, and W. C. Willett. "Intake of Potassium, Magnesium, Calcium, and Fiber and Risk of Stroke Among US Men." Circulation 98.12 (1998): 1198-204. 8 pages.

Assayed, Mohamed E., and A. M. Abd El-Aty. "Cruciferous Plants: Phytochemical Toxicity Versus Cancer Chemoprotection." Mini Reviews in Medicinal Chemistry 9.13 (2009): 1470-478. 9 pages.

Assis, M. C. De, E. R. Rabelo, C. W. Avila, C. A. Polanczyk, and L. E. Rohde. "Improved Oral Anticoagulation After a Dietary Vitamin K-Guided Strategy: A Randomized Controlled Trial." Circulation 120.12 (2009): 1115-122. 12 pages.

Bacon, J. R., et al. "Sulforaphane and Quercetin Modulate PhIP-DNA Adduct Formation in Human HepG2 Cells and Hepatocytes." Carcinogenesis 24.12 (2003): 1903-911. 9 pages.

Bakalova, R., Z. Zhelev, I. Aoki, and T. Saga. "Tissue Redox Activity as a Hallmark of Carcinogenesis: From Early to Terminal Stages of Cancer." Clinical Cancer Research 19.9 (2013): 2503-517. 16 pages.

Baker, Brandon. "Oil Spills Increased by 17% in 2013 >> EcoWatch." EcoWatch. EcoWatch, May 22, 2014. 4 pages.

Bangladesh Cohort. 1 page.

Barillari, Jessica, et al. "Kaiware Daikon (*Raphanus sativus* L.) Extract: A Naturally Multipotent Chemopreventive Agent." Journal of Agricultural and Food Chemistry 56.17 (2008): 7823-830. 8 pages.

Basten, Graham, et al. "Sulforaphane and Its Glutathione Conjugate but Not Sulforaphane Nitrile Induced UDP-glucuronosyl Transferase (UGT1A1) and Gluthione Transferase (GSTA1) in Cultured Cells." Carcinogenesis 23.8 (2002): 1399-404. 6 pages.

Bellostas, Natalia, Iben Lykke Petersen, Jens Christian Sorensen, and Hilmer Sørensen. "A Fast and Gentle Method for the Isolation of Myrosinase Complexes from Brassicaceous Seeds." Journal of Biochemical and Biophysical Methods 70.6 (2008): 918-25. 8 pages.

Benzene Phase I and Phase II. 2 pages.

Benzo(a)pyrene (BaP). Aug. 1, 2007. TEACH Chemical Summary. 14 pages.

Bernardi, Roberta, et al. "Isolation and Biochemical Characterization of a Basic Myrosinase from Ripe Crambe Abyssinica Seeds, Highly Specific for Epi-Progoitrin." Journal of Agricultural and Food Chemistry 51 (2003): 2737-744. 8 pages.

Bestwick, Lara A., et al. "Purification and Characterization of a Nitrilase from Brassica Napus." Physiologia Plantarum 89.4 (1993): 811-16. 7 pages.

Beulens, Joline W.j., Michiel L. Bots, Femke Atsma, Marie-Louise E.I. Bartelink, Matthias Prokop, Johanna M. Geleijnse, Jacqueline C.m. Witteman, Diederick E. Grobbee, and Yvonne T. Van Der Schouw. "High Dietary Menaquinone Intake Is Associated with Reduced Coronary Calicification" Atherosclerosis 203.2 (2009): 489-493 3 pages.

Bheemreddy, Radha M., and Elizabeth H. Jeffery. "The Metabolic Fate of Purified Glucoraphanin in F344 Rats." Journal of Agricultural and Food Chemistry 55.8 (2007): 2861-866. 6 pages.

Bheemreddy, Rhada, et al. "Chapter 34: Glucosinolates." Nutritional Oncology. Elsevier, 2006. 583-96. 14 pages.

Bialecki, Jason, et al. "Collision-induced Dissociationmass Spectra of Glucosinolate Anions." J. Mass. Spectrom. 45 (2010): 272-83. 12 pages.

Blair, Ian A. "Analysis of Endogenous Glutathione-adducts and Their Metabolites." Biomedical Chromatography 24.1 (2010): 29-38. 10 pages.

Bloom, Iris. "Impoundments Leaking: Breaking News Reinforces Three Major Reports on Fracking." Protecting Our Waters. Protecting Our Waters, Aug. 7, 2014. 9 pages.

Boddupalli, Sekhar, et al. "Induction of Phase 2 Antioxidant Enzymes by Broccoli Sulforaphane: perspectives in maintaining the antioxidant activity of vitamins A, C, and E." Frontiers in Genetics 3 (2012): 1-15. 15 pages.

Boekel, Martinus Van, et al. "A Review on the Beneficial Aspects of Food Processing." Molecular Nutrition & Food Research 54.9 (2010): 1215-247. 33 pages.

Bones, Atle M., and John T. Rossiter. "The Enzymic and Chemically Induced Decomposition of Glucosinolates." ChemInform 37.38 (2006): 1053-067. 15 pages.

Bones, Atle M., and John T. Rossiter. "The Myrosinase-glucosinolate System, Its Organisation and Biochemistry." Physiologia Plantarum 97.1 (1996): 194-208. 16 pages.

Boiling, Nigel P., Avril A. B. Robertson, and John J. Morrison. "The Synthesis of Isotopically Labelled Glucosinolates for Analysis and Metabolic Studies." Journal of Labelled Compounds and Radiopharmaceuticals 50.5-6 (2007): 260-63. 4 pages.

Brooks, James, et al. "Potent Induction of Phase 2 Enzymes in Human Prostate Cells by Sulforaphane." Cancer Epidemiol Biomarkers Prev 10 (2001): 949-54. 7 pages.

Brown, Gordon D., and Siamon Gordon. "Fungal β-Glucans and Mammalian Immunity." Immunity 19.3 (2003): 311-15. 5 pages.

Bulka, Catherine, et al. "Residence Proximity to Benzene Release Sites Is Associated with Increased Incidence of Non-Hodgkin Lymphoma." Cancer 119.18 (2013): 3309-317. 9 pages.

Byrne, Mikaela, et al. "Epigenetic modulation in the treatment of atherosclerotic disease." Frontiers in Genetics (2014): 1-7. 7 pages.

Campas-Baypoli, et al. "HPLC Method Validation for Measurement of Sulforaphane Level in Broccoli By-products." Biomedical Chromatography (2009). 6 pages.

Campas-Baypoli, Olga, et al. "Contenido De Sulforafano (1-isotiocianato-4-(metilsulfinil)-butano) En Vegetales Cruciferos." Archivos Latinoamericanos De Nutricion 59.1 (2009): 95-100. 6 pages.

Centers for Disease and Control. Aug. 29, 2005. Benzene Fact Sheet. 4 pages.

Chan, Godfrey, Wing Chan, and Daniel Sze. "The Effects of β-glucan on Human Immune and Cancer Cells." Journal of Hematology & Oncology 2.1 (2009): 25. 11 pages.

Chartoumpekis, Dionysios, and Thomas Kensler. "New Player on an Old Field; the Keap1/Nrf2 Pathway as a Target for Treatment of Type 2 Diabetes and Metabolic Syndrome." Current Diabetes Reviews 9.2 (2013): 137-45. 9 pages.

(56) References Cited

OTHER PUBLICATIONS

Chen, X.-L., et al. "Activation of Nrf2/ARE Pathway Protects Endothelial Cells from Oxidant Injury and Inhibits Inflammatory Gene Expression." AJP: Heart and Circulatory Physiology 290.5 (2006): H1862-1870. 9 pages.

Chiang, William C. K., Donald J. Pusateri, and Richard E. A. Leitz. "Gas Chromatography/Mass Spectrometry Method for the Determination of Sulforaphane and Sulforaphane Nitrile in Broccoli." Journal of Agricultural and Food Chemistry 46.3 (1998): 1018-021. 4 pages.

Choubdar, N., et al. "Supercritical Fluid Chromatography of Myrosinase Reaction Products in Ground YellowMustard Seed Oil." Journal of Food and Science 75.4 (2010): C341-345. 5 pages.

Christopher Wanjek. "Broccoli Brew Eases Air Pollution Effect, But Is This Detox?" (2014). 3 pages.

Chung, Min-Yu. "Molecular Mechanisms of Chemopreventive Phytochemicals against Gastroenterological Cancer Development." World Journal of Gastroenterology 19.7 (2013): 984. 10 pages.

Clariana, Maria, et al. "High Pressure Processing of Swede (*Brassica napus*): Impact on Quality Properties." Innovative Food Science & Emerging Technologies 12.2 (2011): 85-92. 8 pages.

Clarke, Don Brian. "Glucosinolates, Structures and Analysis in Food." Analytical Methods 2.4 (2010): 310-25. 17 pages.

Clarke, John D., Roderick H. Dashwood, and Emily Ho. "Multitargeted Prevention of Cancer by Sulforaphane." Cancer Letters 269.2 (2008): 291-304. 20 pages.

Conzatti, Adriana. "Clinical and Molecular Evidence of the Consumption of Broccoli, Glucoraphanin and Sulforaphane in Humans." Nutr. Hosp. 31.2 (2015): 559-69. 11 pages.

Cornblatt, B. S., et al. "Preclinical and Clinical Evaluation of Sulforaphane for Chemoprevention in the Breast." Carcinogenesis 28.7 (2007): 1485-490. 6 pages.

Cunha, Ana Rosa, Bianca Umbelino, Margarida L. Correia, and Mario Fritsch Neves. "Magnesium and Vascular Changes in Hypertension." International Journal of Hypertension 2012 (2012): 1-7. 7 pages.

Cyanobacterial Toxins: Microcystin-LR in Drinking-water. 1998. World Health Organization. 18 pages.

Damodharan, Umadevi, Ravikumar Ganesan, and Uma C. Radhakrishnan. "Expression of MMP2 and MMP9 (Gelatinases A and B) in Human Colon Cancer Cells." Applied Biochemistry and Biotechnology 165.5-6 (2011): 1245-252. 8 pages.

Das, Biswa Nath, Young-Woo Kim, and Young-Sam Keum. "Mechanisms of Nrf2/Keap1-Dependent Phase II Cytoprotective and Detoxifying Gene Expression and Potential Cellular Targets of Chemopreventive Isothiocyanates." Oxidative Medicine and Cellular Longevity 2013 (2013): 1-7. 8 pages.

Davidson, Rose K., et al. "Sulforaphane Represses Matrix-Degrading Proteases and Protects Cartilage From Destruction In Vitro and In Vivo." Arthritis & Rheumatism 65.12 (2013): 3130-140. 11 pages.

Derry, Molly M., Komal Raina, Chapla Agarwal, and Rajesh Agarwal. "Identifying Molecular Targets of Lifestyle Modifications in Colon Cancer Prevention." Frontiers in Oncology 3 (2013): 1-20. 20 pages.

Dinkova-Kostova, Albena T., and Paul Talalay. "NAD(P)H:quinone Acceptor Oxidoreductase 1 (NQO1), a Multifunctional Antioxidant Enzyme and Exceptionally Versatile Cytoprotector." Archives of Biochemistry and Biophysics 501.1 (2010): 116-23. 18 pages.

Dinkova-Kostova, Albena, et al."Chemical Structures of Inducers of Nicotinamide Quinone Oxidoreductase 1 (NQO1)." Methods in Enzymology. vol. 382. N.p.: Elsevier, n.d. 423-48. 26 pages, 2004.

Dominguez, Ligia, et al. "Magnesium and Muscle Performance in Older Persons: The InCHIANTI Study1—Magnesium and Muscle Performance in Older Persons: The InCHIANTI Study." The American Journal of Clinical Nutrition 84 (2006): 419-26. 8 pages.

Duchateau, G., et al. "Absolute Oral Bioavailability and Metabolic Turnover of -Sitosterol in Healthy Subjects." Drug Metabolism and Disposition 40.10 (2012): 2026-030. 5 pages.

Eades, G., M. Yang, Y. Yao, Y. Zhang, and Q. Zhou. "MiR-200a Regulates Nrf2 Activation by Targeting Keap1 MRNA in Breast Cancer Cells." Journal of Biological Chemistry 286.47 (2011): 40725-0733. 11 pages.

Earthjustice. Oil Refineries: The Infographic. 2014. 4 pages.

Ediage, E. Njumbe, et al. "Screening, Identification and Quantification of Glucosinolates in Black Radish (*Raphanus sativus* L. Niger) Based Dietary Supplements Using Liquid Chromatography Coupled with a Photodiode Array and Liquid Chromatography—Mass Spectrometry." Journal of Chromatography A 1218 28 (2011):4395-405 11 pages.

Egner, P. A., et al. "Bioavailability of Sulforaphane from Two Broccoli Sprout Beverages: Results of a Short-term, Cross-over Clinical Trial in Qidong, China." Cancer Prevention Research 4.3 (2011): 384-95. 13 pages.

Egner, Patricia A., et al."Quantification of Sulforaphane Mercapturic Acid Pathway Conjugates in Human Urine by High-Performance Liquid Chromatography and Isotope-Dilution Tandem Mass Spectrometry." Chemical Research in Toxicology 21.10 (2008): 1991-996. 6 pages.

Egner, Patricia. "Rapid and Sustainable Detoxication of Airborne Pollutants by Broccoli Sprout Beverage: Results of a Randomized Clinical Trial in China." Cancer Prevention Research (2014): 813-23. 12 pages.

Elder, Sonya J., David B. Haytowitz, Juliette Howe, James W. Peterson, and Sarah L. Booth. "Vitamin K Contents of Meat, Dairy, and Fast Food in the U.S. Diet." Journal of Agricultural and Food Chemistry 54.2 (2006): 463-67. 5 pages.

Evans, Paul C. "The Influence of Sulforaphane on Vascular Health and Its Relevance to Nutritional Approaches to Prevent Cardiovascular Disease." The EPMA Journal 2.1 (2011): 9-14. 6 pages.

Eylen, D. Van, el al. "Influence of Pressure/temperature Treatments on Glucosinolate Conversion in Broccoli (*Brassica oleraceae* L. Cv Italica) Heads." Food Chemistry 112.3 (2009): 646-53. 8 pages.

Eylen, David Van, Indrawati Oey, Marc Hendrickx, and Ann Van Loey. "Effects of Pressure/temperature Treatments on Stability and Activity of Endogenous Broccoli (*Brassica oleracea* L. Cv. Italica) Myrosinase and on Cell Permeability." Journal of Food Engineering 89.2 (2008): 178-86. 9 pages.

Fahey, J. W. "Broccoli Sprouts: An Exceptionally Rich Source of Inducers of Enzymes That Protect against Chemical Carcinogens." Proceedings of the National Academy of Sciences 94.19 (1997): 10367-0372. 6 pages.

Fahey, Jed W., and Thomas W. Kensler. "Role of Dietary Supplements/Nutraceuticals in Chemoprevention through Induction of Cytoprotective Enzymes." Chemical Research in Toxicology 20.4 (2007): 572-76. 5 pages.

Fahey, Jed, et al. "The "Prochaska" Microtiter Plate Bioassay for Inducers of NQO1." Methods in Enzymology. vol. 382. N.p. Elsevier, n.d. 243-58. 16 pages, 2004.

Feillet-Coudray, Christine. "Exchangeable Magnesium Pool Masses in Healthy Women: Effects of Magnesium Supplementation." The American Journal of Clinical Nutrition 75 (2002): 72-78. 7 pages.

Finley, Bruce. "Suncor Spill Still Taints South Platte, Proves Benzene a Tough Mop-up." The Denver Post. The Denver Post, May 15, 2013. 6 pages.

Fisher, D., I. J. et al.. "Technology Transfer and Scale Up of a Potential Cancer-Preventive Plant Dynamic Extraction of Glucoraphanin." Journal of Liquid Chromatography & Related Technologies 28.12-13 (2005): 1913-922. 11 pages.

Fiore, R., et al. "Something More to Say about Calcium Homeostasis: The Role of Vitamin K2 in Vascular Calcification and Osteoporosis." European Review for Medical and Pharmacological Sciences (2013): 2433-440. 8 pages.

Fu, Xueyan, Judith Moreines, and Sarah L. Booth. "Vitamin K Supplementation Does Not Prevent Bone Loss in Ovariectomized Norway Rats." Nutrition & Metabolism 9.1 (2012): 12. 5 pages.

Gaikwad, Nilesh W., Eleanor G. Rogan, and Ercole L. Cavalieri. "Evidence from ESI-MS for NQO1-catalyzed Reduction of Estrogen Ortho-quinones." Free Radical Biology and Medicine 43.9 (2007): 1289-298. 19 pages.

(56) References Cited

OTHER PUBLICATIONS

Galgano, F., F. Favati, M. Caruso, A. Pietrafesa, and S. Natella. "The Influence of Processing and Preservation on the Retention of Health-Promoting Compounds in Broccoli." Journal of Food Science 72.2 (2007): S130-135. 6 pages.

Gan, Nanqin, et al. "Sulforaphane Protects Microcystin-LR-induced Toxicity through Activation of the Nrf2-mediated Defensive Response." Toxicology and Applied Pharmacology 247.2 (2010): 129-37. 17 pages.

Garcia, Lisa. "Communities Near Oil Refineries Must Demand Cleaner Air." The Huffington Post. TheHuffingtonPost.com, Aug. 8, 2014. 2 pages.

Gasper, Amy. "Glutathione S-transferase M1 Polymorphism and Metabolism of Sulforaphane from Standard and High-glucosinolate Broccoli." Am J Clin Nutr 82 (2005): 1283-291. 12 pages.

Geleijnse, Johanna, et al. "Dietary Intake of Menaquinone Is Associated with a Reduced Risk of Coronary Heart Disease: The Rotterdam Study." Nutritional Epidemiology (2004): 3100-105. 6 pages.

Gobbo, L. C. Del, F. Imamura, J. H. Wu, M. C. De Oliveira Otto, S. E. Chiuve, and D. Mozaffarian. "Circulating and Dietary Magnesium and Risk of Cardiovascular Disease: A Systematic Review and Meta-analysis of Prospective Studies." American Journal of Clinical Nutrition 98.1 (2013): 160-73. 14 pages.

Goldring, M. B. "Chondrogenesis, Chondrocyte Differentiation, and Articular Cartilage Metabolism in Health and Osteoarthritis." Therapeutic Advances in Musculoskeletal Disease 4.4 (2012): 269-85. 17 pages.

Grabacka, Maja, et al. "Phytochemical Modulators of Mitochondria: The Search for Chemopreventive Agents and Supportive Therapeutics." Pharmaceuticals (2014): 913-42. 30 pages.

GRAS Associates, LLC. Feb. 25, 2008. Natto Pharma GRAS submission for NK7. 180 pages.

Gratacós-Cubarsí, et al. "Simultaneous Evaluation of Intact Glucosinolates and Phenolic Compounds by UPLC-DAD-MS/MS in *Brassica oleracea* L. Var. Botrytis." Food Chemistry 121.1 (2010): 257-63. 7 pages.

Grattan, Bruce. "Plant Sterols as Anticancer Nutrients: Evidence for Their Role in Breast Cancer." Nutrients 5.2 (2013): 359-87. 29 pages.

Gray, Michael, et al. "Development of Liquid Chromatography/mass Spectrometry Methods for the Quantitative Analysis of Herbal Medicine in Biological Fl Uids: A Review." Biomedical Chromatography 24 (2010): 91-103. 13 pages.

Grubb, C. Douglas, and Steffen Abel. "Glucosinolate Metabolism and Its Control." Trends in Plant Science 11.2 (2006): 89-100. 12 pages.

Gueron, G., et al. "Critical Role of Endogenous Heme Oxygenase 1 as a Tuner of the Invasive Potential of Prostate Cancer Cells." Molecular Cancer Research 7.11 (2009): 1745-755. 12 pages.

Gurule, Kendall. "BTEX and Fracking." BTEX and Fracking. FrackWire, Jul. 31, 2013. 6 pages.

Hanlon, Natalya, et al. "Absolute Bioavailability and Dose-dependent Pharmacokinetic Behaviour of Dietary Doses of the Chemopreventive Isothiocyanate Sulforaphane in Rat." British Journal of Nutrition 99.03 (2008). 6 pages.

Hauder, Johanna, et al. "LC-MS/MS Quantification of Sulforaphane and Indole-3-carbinol Metabolites in Human Plasma and Urine after Dietary Intake of Selenium-Fortified Broccoli." Journal of Agricultural and Food Chemistry 59.15 (2011): 8047-057. 11 pages.

Hauser, Ross. "The Acceleration of Articular Cartilage Degeneration in Osteoarthritis by Nonsteroidal Anti-inflammatory Drugs." Journal of Prolotherapy 2.1 (2010): 305-22. 18 pages.

Hayes, John D., Michael O. Kelleher, and Ian M. Eggleston. "The Cancer Chemopreventive Actions of Phytochemicals Derived from Glucosinolates." European Journal of Nutrition 47.S2 (2008): 73-88. 16 pages.

Heath, David. "Even Low Doses of Arsenic Trigger Cancer in Mice, Study Finds." The Center for Public Inegrity, Jul. 8, 2014. 5 pages.

Higdon, J., B. Delage, D. Williams, and R. Dashwood. "Cruciferous Vegetables and Human Cancer Risk: Epidemiologic Evidence and Mechanistic Basis." Pharmacological Research 55.3 (2007): 224-36. 22 pages.

Ho, Jin-Nyoung, Eun-Ryung Kang, Ho-Geun Yoon, Hyelin Jeon, Woojin Jun, Ronald R. Watson, and Jeongmin Lee. "Inhibition of Premature Death by Isothiocyanates through Immune Restoration in LP-BM5 Leukemia Retrovirus-Infected C57BL/6 Mice." Bioscience, Biotechnology, and Biochemistry 75.7 (2011): 1234-1239 6 pages.

Hoh, C., et al. "Pilot Study of Oral Silibinin, a Putative Chemopreventive Agent, in Colorectal Cancer Patients: Silibinin Levels in Plasma, Colorectum, and Liver and Their Pharmacodynamic Consequences." Clinical Cancer Research 12.9 (2006): 2944-950. 8 pages.

Houghton, Christine A., Robert G. Fassett, and Jeff S. Coombes. "Sulforaphane: Translational Research from Laboratory Bench to Clinic." Nutrition Reviews 71.11 (2013): 709-26. 18 pages.

Houston Regional Benzene Air Pollution Reduction: A Voluntary Plan for Major Sources. Feb. 2007. Mayor's Office of Environmental Programming Department of Health and Human Services Bureau of Air Quality Control. 48 pages.

Hruby, A., et al. "Higher Magnesium Intake Is Associated with Lower Fasting Glucose and Insulin, with No Evidence of Interaction with Select Genetic Loci, in a Meta-Analysis of 15 CHARGE Consortium Studies." Journal of Nutrition 143.3 (2013): 345-53. 9 pages.

Hu, R. "In Vivo Pharmacokinetics and Regulation of Gene Expression Profiles by Isothiocyanate Sulforaphane in the Rat." Journal of Pharmacology and Experimental Therapeutics 310.1 (2004): 263-71. 9 pages.

Hunt, Curtiss. "Magnesium Requirements: New Estimations for Men and Women by Cross-sectional Statistical Analyses of Metabolic Magnesium Balance Data." The American Journal of Clinical Nutrition (2006): 843-52. 10 pages.

Ichikawa, T., K. Horie-Inoue, K. Ikeda, B. Blumberg, and S. Inoue. "Vitamin K2 Induces Phosphorylation of Protein Kinase A and Expression of Novel Target Genes in Osteoblastic Cells." Journal of Molecular Endocrinology 39.4 (2007): 239-47. 9 pages.

Ishida, Masahiko, Tomohiro Kakizaki, Takayoshi Ohara, and Yasujiro Morimitsu. "Development of a Simple and Rapid Extraction Method of Glucosinolates from Radish Roots." Breeding Science 61.2 (2011): 208-11. 4 pages.

Iskander, K., J. Li, S. Han, B. Zheng, and A. K. Jaiswal. "NQO1 and NQO2 Regulation of Humoral Immunity and Autoimmunity." Journal of Biological Chemistry 281.41 (2006): 30917-0924. 9 pages.

Iwamoto, Jun, Tsuyoshi Takeda, and Yoshihiro Sato. "Effects of Vitamin K2 on Osteoporosis." Current Pharmaceutical Design 10.21 (2004): 2557-576. 2 pages.

Jeffery, E.h., et al. "Variation in Content of Bioactive Components in Broccoli." Journal of Food Composition and Analysis 16.3 (2003): 323-30. 8 pages.

Jin, Kyubok, Kyubok, Tae Hee Kim, Yeong Hoon Kim, and Yang Wook Kim. "Additional Antihypertensive Effect of Magnesium Supplementation with an Angiotensin II Receptor Blocker in Hypomagnesemic Rats." The Korean Journal of Internal Medicine 28.2 (2013): 197. 9 pages.

Juurlink, Bernhard, et al. "Hydroxybenzoic Acid Isomers and the Cardiovascular System." Nutrition Journal 13.63 (2014): 1-10. 10 pages.

Jwanny, E.w., et al. "Myrosinase from Roots of Raphanus Sativus." Phytochemistry 39.6 (1995): 1301-303. 3 pages.

Kaczor, Tina. "Calcium and Cardiovascular Risk: The Devil is in the Details." (2013): 6 pages.

Kensler, T. W., et al. "Modulation of the Metabolism of Airborne Pollutants by Glucoraphanin-rich and Sulforaphane-rich Broccoli Sprout Beverages in Qidong, China." Carcinogenesis 33.1 (2011): 101-07. 7 pages.

Kensler, Thomas. "Keap1-Nrf2 Signaling: A Target for Cancer Prevention by Sulforaphane." Top Curr Chem. 329 (2013): 163-77. Web.

Kestwal, Rakesh Mohan, Jia Ching Lin, Dipali Bagal-Kestwal, and Been Huang Chiang. "Glucosinolates Fortification of Cruciferous

(56) References Cited

OTHER PUBLICATIONS

Sprouts by Sulphur Supplementation during Cultivation to Enhance Anti-cancer Activity." Food Chemistry 126.3 (2011): 1164-171. 8 pages.

Keum, Y.-S. "Mechanism of Action of Sulforaphane: Inhibition of P38 Mitogen-Activated Protein Kinase Isoforms Contributing to the Induction of Antioxidant Response Element-Mediated Heme Oxygenase-1 in Human Hepatoma HepG2 Cells." Cancer Research 66.17 (2006): 8804-813. 11 pages.

Khan, A. M., S. A. Lubitz, L. M. Sullivan, J. X. Sun, D. Levy, R. S. Vasan, J. W. Magnani, P. T. Ellinor, E. J. Benjamin, and T. J. Wang. "Low Serum Magnesium and the Development of Atrial Fibrillation in the Community: The Framingham Heart Study." Circulation 127.1 (2013): 33-38. 6 pages.

Kim, D. J., P. Xun, K. Liu, C. Loria, K. Yokota, D. R. Jacobs, and K. He. "Magnesium Intake in Relation to Systemic Inflammation, Insulin Resistance, and the Incidence of Diabetes." Diabetes Care 33.12 (2010): 2604-610. 7 pages.

Kim, H. Ah, Y. Yeo, W.-U. Kim, and S. Kim. "Phase 2 Enzyme Inducer Sulphoraphane Blocks Matrix Metalloproteinase Production in Articular Chondrocytes." Rheumatology 48.8 (2009): 932-38. 7 pages.

Kim, H.-A., et al. "Phase 2 Enzyme Inducer Sulphoraphane Blocks Prostaglandin and Nitric Oxide Synthesis in Human Articular Chondrocytes and Inhibits Cartilage Matrix Degradation." Rheumatology 51.6 (2012): 1006-016. 11 pages.

Kissen, Ralph, John T. Rossiter, and Atle M. Bones. "The 'mustard Oil Bomb': Not so Easy to Assemble?! Localization, Expression and Distribution of the Components of the Myrosinase Enzyme System." Phytochemistry Reviews 8.1 (2009): 69-86. 18 pages.

Klevay, Leslie, et al. "Low Dietary Magnesium Increases Supraventricular Ectopy." The American Journal of Clinical Nutrition (2002): 550-54. 5 pages.

Kliebenstein, Dan J., Juergen Kroymann, and Thomas Mitchell-Olds. "The Glucosinolate-myrosinase System in an Ecological and Evolutionary Context." Current Opinion in Plant Biology 8.3 (2005): 264-71. 8 pages.

Kodama, Noriko, Kiyoshi Komuta, Norio Sakai, and Hiroaki Nanba. "Effects of D-Fraction, a Polysaccharide from Grifola Frondosa on Tumor Growth Involve Activation of NK Cells." Biological & Pharmaceutical Bulletin 25.12 (2002): 1647-650. 4 pages.

Kong, Jin-Sun, et al. "Inhibition of Synovial Hyperplasia, Rheumatoid T Cell Activation, and Experimental Arthritis in Mice by Sulforaphane, a Naturally Occurring Isothiocyanate."Arthritis & Rheumatism 62.1 (2010): 159-70. 12 pages.

Kortz, Linda, Christin Helmschrodt, and Uta Ceglarek. "Fast Liquid Chromatography Combined with Mass Spectrometry for the Analysis of Metabolites and Proteins in Human Body Fluids." Analytical and Bioanalytical Chemistry 399.8 (2011): 2635-644. 10 pages.

Kuiper, Heather. "LC-MS/MS Quantitation of Mercapturic Acid Conjugates of Lipid Peroxidation Products as Markers of Oxidative Stress." Current Protocols in Toxicology (2010). 17 pages.

Kumar, Anoop, and Gabriele Sabbioni. "New Biomarkers for Monitoring the Levels of Isothiocyanates in Humans." Chemical Research in Toxicology 23.4 (2010): 756-65. 10 pages.

Kupetsky-Rincon, Erine A., and Jouni Uitto. "Magnesium: Novel Applications in Cardiovascular Disease—A Review of the Literature." Annals of Nutrition and Metabolism 61.2 (2012): 102-10. 9 pages.

Lee, Jong Suk, et al. "Grifola Frondosa Water Extract Alleviates Intestinal Inflammation by Suppressing TNF-a Production and Its Signaling." Experimental and Molecular Medicine42.2 (2010): 143. 12 pages.

Lee, Kim-Chung, et al. "Rapid Screening Method for Intact Glucosinolates in Chinese Medicinal Herbs by Using Liquid Chromatography Coupled with Electrospray Ionization Ion Trap Mass Spectrometry in Negative Ion Mode." Rapid Communications in Mass Spectrometry 22.18 (2008): 2825-834. 10 pages.

Levy, Robert. "Potential Treatment of Calciphylaxis with Vitamin K2: Comment on the Article by Jacobs-Kosmin and DeHoratius." Arthritis & Rheumatism 57.8 (2007): 1575-576. 2 pages.

Lewis, J., et al. "Glucosinolate Content of Brassica Vegetables: Analysis of Twenty-Four Cultivars of Calabrese (green Sprouting Broccoli, Brassica o/eracea L. Var. Botrytis Subvar, Cymosa Lain.)." Food Chemistry 25 (1987): 259-68. 10 pages.

Li, Xian, and Mosbah M. Kushad. "Purification and Characterization of Myrosinase from Horseradish (Armoracia rusticana) Roots." Plant Physiology and Biochemistry 43.6 (2005): 503-11. 9 pages.

Li, Y., T. Zhang, H. Korkaya, S. Liu, H. F. Lee, B. Newman, Y. Yu, S. G. Clouthier, S. J. Schwartz, M. S. Wicha, and D. Sun. "Sulforaphane, a Dietary Component of Broccoli/Broccoli Sprouts, Inhibits Breast Cancer Stem Cells."Clinical Cancer Research 16.9 (2010): 2580-590. 12 pages.

Liang, H., Q. Yuan, and Q. Xiao. "Purification of Sulforaphane from Brassica Oleracea Seed Meal Using Low-pressure Column Chromatography." Journal of Chromatography B 828.1-2 (2005): 91-96. 6 pages.

Liang, Hao, Chunfang Li, Qipeng Yuan, and Frank Vriesekoop. "Separation and Purification of Sulforaphane from Broccoli Seeds by Solid Phase Extraction and Preparative High-Performance Liquid Chromatography." Journal of Agricultural and Food Chemistry 55.20 (2007): 8047-053. 7 pages.

Liang, Hao, Cuijuan Li, Qipeng Yuan, and Frank Vriesekoop. "Application of High-Speed Countercurrent Chromatography for the Isolation of Sulforaphane from Broccoli Seed Meal." Journal of Agricultural and Food Chemistry 56.17 (2008): 7746-749. 4 pages.

Lin, Che-Yi, et al. "Cytochrome P450 Metabolism of Betel Quid-Derived Compounds: Implications for the Development of Prevention Strategies for Oral and Pharyngeal Cancers." The Scientific World Journal 2013 (2013): 1-11. 11 pages.

Loguercio, Carmela. "Silybin and the Liver: From Basic Research to Clinical Practice." World Journal of Gastroenterology 17.18 (2011): 2288. 14 pages.

Lombardi, Kristen. "'Upset' Emissions: Flares in the Air, Worry on the Ground." Center for Public Integrity. N.p., May 21, 2013. 16 pages.

Long, Samantha, et al. "Role of Cellular Magnesium in Human Diseases." Austin J Nutr Food Sci. 2.10 (n.d.): 1-19. 19 pages, 2014.

Lotz, M., et al. "Value of Biomarkers in Osteoarthritis: Current Status and Perspectives." Annals of the Rheumatic Diseases 72.11 (2013): 1756-763. 10 pages.

Lukaski, Henry. "Dietary Magnesium Depletion Affects Metabolic Responses during Submaximal Exercise in Postmenopausal Women." The Journal of Nutrition (2002): 930-35. 6 pages.

Lusin, Trdan, et al. Abstract of "Evaluation of Bisphenol a Glucuronidation According ToUTG1A1*28 Polymorphism by a New LC-MS/MS Assay." Toxicology 292 (2011): 33-41. 1 page.

Malaguti, M., C. Angeloni, N. Garatachea, M. Baldini, E. Leoncini, P. S. Collado, G. Teti, M. Falconi, J. Gonzalez-Gallego, and S. Hrelia. "Sulforaphane Treatment Protects Skeletal Muscle against Damage Induced by Exhaustive Exercise in Rats." Journal of Applied Physiology 107.4 (2009): 1028-036. 10 pages.

Manjanna, K. M., B. Shivakumar, and T. M. Pramod Kumar. "Microencapsulation: An Acclaimed Novel Drug-Delivery System for NSAIDs in Arthritis." Critical Reviews™ in Therapeutic Drug Carrier Systems 27.6 (2010): 509-45. 37 pages.

Martin, Andrew. "Antibacterial Chemical Raises Safety Issues." The New York Times, The New York Times, Aug. 19, 2011. 3 pages.

Matusheski, Nathan V., and Elizabeth H. Jeffery. "Comparison of the Bioactivity of Two Glucoraphanin Hydrolysis Products Found in Broccoli, Sulforaphane and Sulforaphane Nitrile." Journal of Agricultural and Food Chemistry 49.12 (2001): 5743-749. 7 pages.

Matusheski, Nathan V., John A. Juvik, and Elizabeth H. Jeffery. "Heating Decreases Epithiospecifier Protein Activity and Increases Sulforaphane Formation in Broccoli." Phytochemistry 65.9 (2004): 1273-281. 9 pages.

Matusheski, Nathan, et al. "Preparative HPLC Method for the Purification of Sulforaphane and Sulforaphane Nitrile from Brassica Oleracea." J. Agric. Food Chem 49 (2001): 1867-872. 6 pages.

(56) References Cited

OTHER PUBLICATIONS

Mays, Jared R., et al. "Identification, Synthesis, and Enzymology of Non-natural Glucosinolate Chemopreventive Candidates." ChemBioChem 9.5 (2008): 729-47. 9 pages.
Mccann, J. C., and B. N. Ames. "Vitamin K, an Example of Triage Theory: Is Micronutrient Inadequacy Linked to Diseases of Aging?" American Journal of Clinical Nutrition 90.4 (2009): 889-907. 19 pages.
Mckenna, Gregory J., et al. "A Role for Matrix Metalloproteinases and Tumor Host Interaction in Hepatocellular Carcinomas." The American Journal of Surgery 183.5 (2002): 588-94. 7 pages.
Meyer, Michael, and Sieghard T. Adam. "Comparison of Glucosinolate Levels in Commercial Broccoli and Red Cabbage from Conventional and Ecological Farming." European Food Research and Technology 226.6 (2008): 1429-437. 9 pages.
Miller, Mike. Environmental Protection Agency. Benzene. 1 page.
Misialek, Jeffrey R., Faye L. Lopez, Pamela L. Lutsey, Rachel R. Huxley, James M. Peacock, Lin Y. Chen, Elsayed Z. Soliman, Sunil K. Agarwal, and Alvaro Alonso. "Serum and Dietary Magnesium and Incidence of Atrial Fibrillation in Whites and in African Americans." Circulation Journal 77.2 (2013): 323-29, 7 pages.
Mohn, Tobias, Brian Cutting, Beat Ernst, and Matthias Hamburger. "Extraction and Analysis of Intact Glucosinolates—A Validated Pressurized Liquid Extraction/liquid Chromatography—mass Spectrometry Protocol for Isatis Tinctoria, and Qualitative Analysis of Other Cruciferous Plants." Journal of Chromatography A 11661-2 (2007): 142-51 10 pages.
Mohn, Tobias, et al. "Glucosinolate Pattern in Isatis Tinctoria and I. Indigotica Seeds." Planta Med 74 (2008): 885-88. 4 pages.
Mohn, Tobias, et al. Supporting Information. "Glucosinolate Pattern in Isatis Tinctoria and I. Indigotica Seeds." Planta Med 74 (2008): E704-706. 3 pages.
Mohn, Tobias. Supplementary Material: Extraction and Quantitative Analysis of Intact Glucosinolates in Plant Extracts—A Validated Pressurized Liquid Extraction/LC-MS Protocol. 3 pages.
Montaut, Sabine, et al. "Updated Glucosinolate Profile of Dithyrea Wislizenii." J. Nat. Prod. 72 (2009): 889-93. 5 pages.
Montgomery, Jeff. "EPA Seeks Tighter Rein on Refinery Toxic Air Releases." Delaware Online, May 15, 2014. 3 pages.
Moreno, D.a., M. Carvajal, C. López-Berenguer, and C. Garcia-Viguera. "Chemical and Biological Characterisation of Nutraceutical Compounds of Broccoli." Journal of Pharmaceutical and Biomedical Analysis 41.5 (2006): 1508-522. 15 pages.
Morra, Matthew J., and Vladimir Borek. "Glucosinolate Preservation in Stored Brassicaceae Seed Meals." Journal of Stored Products Research 46.2 (2010): 98-102. 5 pages.
Morre, D. James, Sara Dick, Elena Bosneaga, Andrew Balicki, L.y. Wu, Nicole Mcclain, and Dorothy M. Morre. "TNOX (ENOX2) Target for Chemosensitization-Low-Dose Responses in the Hormetic Concentration Range." American Journal of Pharmacology and Toxicology 3.1 (2008): 19-29. 11 pages.
Morris, Jim, et al. "Fracking the Eagle Ford Shale."—Big Oil and Bad Air on the Texas Prairie. The Weather Channel. 60 pages, Accesssed Jul. 17, 2014.
Morrison, John J., and Nigel P. Botting. "The Synthesis of Isotopically Labelled Glucoraphanin for Metabolic Studies." Tetrahedron Letters 48.11 (2007): 1891-894. 4 pages.
Muller, Caroline. "Interactions between Glucosinolate- and Myrosinasecontaining Plants and the Sawfly Athalia Rosae." Phytochem Rev 8 (2009): 121-34. 14 pages.
Munday, R., et al. "Inhibition of Urinary Bladder Carcinogenesis by Broccoli Sprouts." Cancer Research 68.5 (2008): 1593-600. 9 pages.
Nakagawa, Kiyotaka, et al. "Evaporative Light-Scattering Analysis of Sulforaphane in Broccoli Samples: Quality of Broccoli Products Regarding Sulforaphane Contents." Journal of Agricultural and Food Chemistry 54.7 (2006): 2479-483. 5 pages.
Nakamura, Yasushi, et al. "Comparison of the Glucosinolate-Myrosinase Systems among Daikon (*Raphanus sativus*, Japanese White Radish) Varieties." Journal of Agricultural and Food Chemistry 56.8 (2008): 2702-707. 6 pages.

Navarro, S. L., et al. "Cruciferous Vegetable Feeding Alters UGT1A1 Activity: Diet- and Genotype-Dependent Changes in Serum Bilirubin in a Controlled Feeding Trial." Cancer Prevention Research 2.4 (2009): 345-52. 16 pages.
Nelson, Chad, et al. "Protection against 2-Hydroxyamino-1-methyl-6-phenylimidazo[4,5-B]pyridine Cytotoxicity and DNA Adduct Formation in Human Prostate Glutathione S-Transferase P1." Cancer Research 61 (2001): 103-09. 8 pages.
Nicoll, Rachel. "A Review of the Effect of Diet on Cardiovascular Calcification." International Journal of Molecular Sciences (2015): 8861-883. 23 pages.
Nimptsch, K., S. Rohrmann, R. Kaaks, and J. Linseisen. "Dietary Vitamin K Intake in Relation to Cancer Incidence and Mortality: Results from the Heidelberg Cohort of the European Prospective Investigation into Cancer and Nutrition (EPIC-Heidelberg)." American Journal of Clinical Nutrition 91.5 (2010): 1348-358 11 pages.
Nimptsch, Katharina, et al. "Dietary Intake of Vitamin K and Risk of Prostate Cancer in the Heidelberg Cohort of the European Prospective Investigation into Cancer and Nutrition (EPIC-Heidelberg)." The American Journal of Clinical Nutrition 87 (2008): 985-82. 8 pages.
Noyan-Ashraf, Mohammad, et al. "Dietary Approaches to Positively Influence Fetal Determinants of Adult Health." The FASEB Journal (2005): 17 pages.
Oil Spills in the United States, 2009-2012. 2 pages.
Pan, Hong, et al. "Sulforaphane Protects Rodent Retinas against Ischemia-Reperfusion Injury through the Activation of the Nrf2/HO-1 Antioxidant Pathway." PLOS One (2014): 1-24. 24 pages.
Pang, Qiuying, et al. "Characterization of Glucosinolate-myrosinase System in Developing Salt Cress Thellungiella Halophila." Physiologia Plantarum 136 (2009): 1-9. 9 pages.
Paolini, M., et al. "Induction of Cytochrome P450, Generation of Oxidative Stress and in Vitro Cell-transforming and DNA-damaging Activities by Glucoraphanin, the Bioprecursor of the Chemopreventive Agent Sulforaphane Found in Broccoli." Carcinogenesis 25.1 (2004): 61-67. 7 pages.
Peterson, Alan. "Vitamin K—Much More Than a Coagulation Vitamin." The Journal of Lancaster General Hospital 3.3 (2008): 112-13. 2 pages.
Petri, N. "Absorption/metabolism Of Sulforaphane And Quercetin, And Regulation Of Phase II Enzymes, In Human Jejunum In Vivo." Drug Metabolism and Disposition 31.6 (2003): 805-13. 9 pages.
Prakash, Dhan, and Charu Gupta. "Glucosinolates: The Phytochemicals of Nutraceutical Importance." Journal of Complementary and Integrative Medicine 9.1 (2012): 17 pages.
Pratheeshkumar, et al. "Quercetin Inhibits Angiogenesis Mediated Human Prostate Tumor Growth by Targeting VEGFR-2 Regulated AKT/mTOR/P70S6K Signaling Pathways." Ed. Subhash Gautam. PLoS ONE7.10 (2012): E47516. 10 pages.
Prestera, Tory, et al. "Comprehensive Chromatographic and Spectroscopic Methods for the Separation and Identification of Intact Glucosinolates." Analytical Biochemistry 239.2 (1996): 168-79. 12 pages.
Rafii, Mahroukh, et al. "Measurement of Homocysteine and Related Metabolites in Human Plasma and Urine by Liquid Chromatography Electrospray Tandem Mass Spectrometry." Journal of Chromatography B 877.28 (2009): 3282-291. 10 pages.
Rangkadilok, N., et al. "The Effect of Post-Harvest and Packaging Treatments on Glucoraphanin Concentration in Broccoli (*Brassica oleracea* Var. Italica)." Journal of Agricultural and Food Chemistry 50 (2002): 7386-391. 6 pages.
Rappaport, Stephen M., et al. "Evidence That Humans Metabolize Benzene via Two Pathways." Environmental Health Perspectives (2009): 947-952. 7 pages.
Ritz, S. A., J. Wan, and D. Diaz-Sanchez. "Sulforaphane-stimulated Phase II Enzyme Induction Inhibits Cytokine Production by Airway Epithelial Cells Stimulated with Diesel Extract." AJP: Lung Cellular and Molecular Physiology292.1 (2006): L33-39. 7 pages.
Rosanoff, Andrea, Connie M. Weaver, and Robert K. Rude. "Suboptimal Magnesium Status in the United States: Are the Health Consequences Underestimated?" Nutrition Reviews 70.3 (2012): 153-64. 12 pages.

(56) References Cited

OTHER PUBLICATIONS

Rowell, Andy. "Crude by Rail Spills Increased 10 Times from 2008-2013—Oil Change International." Oil Change International. Oil Change International, Mar. 26, 2014. 4 pages.
Rubenfire, Adam. "Extra Pay for Pollution?" Wall Street Journal. Wall Street Journal, Jul. 15, 2014. 2 pages.
Rushworth, Stuart, et al. "Lipopolysaccharide-Induced Expression of NAD(P)H:Quinone Oxidoreductase 1 and Heme Oxygenase-1 Protects against Excessive Inflammatory Responses in Human Monocytes." The Journal of Immunology 181 (2008): 6730-737. 9 pages.
Rychlik, Michael, and Sieghard T. Adam. "Glucosinolate and Folate Content in Sprouted Broccoli Seeds." European Food Research and Technology 226.5 (2008): 1057-064. 8 pages.
Sato, Toshiro, Leon J. Schurgers, and Kazuhiro Uenishi. "Comparison of Menaquinone-4 and Menaquinone-7 Bioavailability in Healthy Women." Nutrition Journal 11.1 (2012): 93. 4 pages.
Schemmer, Peter. "Sulforaphane Protects Hearts from Early Injury after Experimental Transplantation." Annals of Transplantation 18 (2013): 558-66. 9 pages.
Schouten, Rob E., et al. "Modelling the Level of the Major Glucosinolates in Broccoli as Affected by Controlled Atmosphere and Temperature." Postharvest Biology and Technology 53.1-2 (2009): 1-10. 10 pages.
Schurgers, Leon, et al. "Vitamin K-containing Dietary Supplements: Comparison of Synthetic Vitamin K 1 and Natto-derived Menaquinone-7." Blood 109.8 (2007): 3279-283. 6 pages.
Shankar, S., et al. "Sulforaphane Enhances the Therapeutic Potential of TRAIL in Prostate Cancer Orthotopic Model through Regulation of Apoptosis, Metastasis, and Angiogenesis." Clinical Cancer Research 14.21 (2008): 6855-866. 13 pages.
Shanmugam, Muthu K., et al. "Ursolic Acid Inhibits Multiple Cell Survival Pathways Leading to Suppression of Growth of Prostate Cancer Xenograft in Nude Mice." Journal of Molecular Medicine89.7 (2011): 713-27. 15 pages.
Shanmugam, Muthu K., et al. "Ursolic Acid Inhibits the Initiation, Progression of Prostate Cancer and Prolongs the Survival of TRAMP Mice by Modulating Pro-Inflammatory Pathways." Ed. Ganesh Chandra Jagetia. PLoS ONE 7.3 (2012): E32476. 9 pages.
Sharan, Rajeshwar N., Ravi Mehrotra, Yashmin Choudhury, and Kamlesh Asotra. "Association of Betel Nut with Carcinogenesis: Revisit with a Clinical Perspective." Ed. Sudha Agarwal. PLoS ONE 7.8 (2012): E42759. 21 pages.
Shea, M. K., and R. M. Holden. "Vitamin K Status and Vascular Calcification: Evidence from Observational and Clinical Studies." Advances in Nutrition: An International Review Journal 3.2 (2012): 158-65. 8 pages.
Shea, M. K., C. J. O'donnell, C. Vermeer, E. J. P. Magdeleyns, M. D. Crosier, C. M. Gundberg, J. M. Ordovas, S. B. Kritchevsky, and S. L. Booth. "Circulating Uncarboxylated Matrix Gla Protein is Associated with Vitamin K Nutritional Status, but Not Coronary Artery Calcium, in Older Adults." Journal of Nutrition, 141: 8 (2011):1529-534. 6 pages.
Shea, M. K., C. J. O'donnell, U. Hoffmann, G. E. Dallal, B. Dawson-Hughes, J. M. Ordovas, P. A. Price, M. K. Williamson, and S. L. Booth. "Vitamin K Supplementation and Progression of Coronary Artery Calcium in Older Men and Women." American Journal of Clinical Nutrition 89.6 (2009): 1799-807. 9 pages.
Shechter, M., M. Sharir, M. J. P. Labrador, J. Forrester, B. Silver, and C. N. Bairey Merz. "Oral Magnesium Therapy Improves Endothelial Function in Patients With Coronary Artery Disease." Circulation 102.19 (2000): 2353-358. 7 pages.
Shen, Lianqing, Guangyao Su, Xiangyang Wang, Qizhen Du, and Kuiwu Wang. "Endogenous and Exogenous Enzymolysis of Vegetable-sourced Glucosinolates and Influencing Factors." Food Chemistry 119.3 (2010): 987-94. 8 pages.
Shinkai, Yasuhiro, Daigo Sumi, Ikuo Fukami, Tetsuro Ishii, and Yoshito Kumagai. "Sulforaphane, an Activator of Nrf2, Suppresses Cellular Accumulation of Arsenic and Its Cytotoxicity in Primary Mouse Hepatocytes." FEBS Letters 580.7 (2006): 1771-774. 4 pages.

Shroff, R., F. Vergara, A. Muck, A. Svatos, and J. Gershenzon. "Non-uniform Distribution of Glucosinolates in Arabidopsis Thaliana Leaves Has Important Consequences for Plant Defense." Proceedings of the National Academy of Sciences 105.16 (2008): 6196-201. 6 pages.
Shulman, Seth. "Ohio Fire Disaster Spotlights Need for Fracking Info (Op-Ed)." LiveScience, TechMedia Network, Jul. 30, 2014. 5 pages.
Singh, et al. Supporting Information. "Sulforaphane Treatment of Autism Spectrum Disorder (ASD)." Sulforaphane Treatment of Autism Spectrum Disorder (ASD). PNAS. 7 pages.
Singh, Kanwaljit, et al. "Sulforaphane Treatment of Autism Spectrum Disorder (ASD)." PNAS. 6 pages.
Sivakumar, G., A. Aliboni, and L. Bacchetta. "HPLC Screening of Anti-cancer Sulforaphane from Important European *Brassica* Species." Food Chemistry 104.4 (2007): 1761-764. 4 pages.
Smiechowska, Anna, Agnieszka Bartoszek, and Jacek Namiesnik. "Determination of Glucosinolates and Their Decomposition Products—Indoles and Isothiocyanates in Cruciferous Vegetables." Critical Reviews in Analytical Chemistry 40.3 (2010): 202-16. 16 pages.
Smith, Martyn, et al. "Hydroquinon, a Benzene Metabolite, Increases the Level of Aneusomy of Chromosome 7 and 8 in Human CD43-positive Progenitor Cells." Carcinogenesis 21.8 (2000): 1485-490. 6 pages.
Song, Lijiang, et al. "Purification of Major Glucosinolates from Brassicaceae Seeds and Preparation of Isothiocyanate and Amine Metabolites." Journal of the Science of Food and Agriculture 86 (2006): 1271-280. 10 pages.
Song, Lijiang, John J. Morrison, Nigel P. Botting, and Paul J. Thornalley. "Analysis of Glucosinolates, Isothiocyanates, and Amine Degradation Products in Vegetable Extracts and Blood Plasma by LC-MS/MS." Analytical Biochemistry 347.2 (2005): 234-43. 10 pages.
Song, Yiqing, et al. "Magnesium Intake and Plasma Concentrations of Markers of Systemic Inflammation and Endothelial Dysfunction in Women." The American Journal of Clinical Nutrition 85 (2007): 1068-074. 7 pages.
Soraghan, Mike. "U.S. Well Sites in 2012 Discharged More than Valdez," WyoFile. WyoFile, Jul. 9, 2013. 6 pages.
Spronk, H. M.h. "Vitamin K Epoxide Reductase Corhplex and Vascular Calcification: Is This the Important Link Between Vitamin K and the Arterial Vessel Wall?" Circulation 113.12 (2006): 1550-552. 4 pages.
Spronk, H.m.h., B.A.m. Soute, L.j. Schurgers, H.h.w. Thijssen, J.g.r. De Mey, and C. Vermeer. "Tissue-Specific Utilization of Menaquinone-4 Results in the Prevention of Arterial Calcification in Warfarin-Treated Rats." Journal of Vascular Research 40.6 (2003): 531-37. 7 pages.
Starrett, Warren, et al. "Sulforaphane Inhibits De Novo Synthesis OflL-8 and MCP-I in Human Epithelial Cells Generated by Cigarette Smoke Extract." Journal of Immunotollicology 8.2 (2011): 150-58. 9 pages.
Stephanz, Hannah. "The Need to Fight for Michigan's Dirtiest Zip Code." Earthjustice, Aug. 11, 2014. 3 pages.
Stevens, Jan F., and Claudia S. Maier. "Acrolein: Sources, Metabolism, and Biomolecular Interactions Relevant to Human Health and Disease." Molecular Nutrition & Food Research 52.1 (2008): 7-25. 34 pages.
Sticher, Otto, and Matthias Hamburger. Albert Hofmann (1906-2008)—an Obituary. 3 pages.
Stoewsand, G. S. "Bioactive Organosulfur Phytochemicals in Brassica Aleracea Vegetables—A Review." Fd Chem. Toxic. 33.6 (1995): 527-43. 7 pages.
Suter, K., T. Mohn, and M. Hamburger. "Seasonal Changes of Glucosinolates in Isatis Leaves, and Effect of Harvest Regimen and Post-harvest Treatment." Planta Medica 73.09 (2007). 6 pages.
Suzuki, Chise, et al. "Behavior of Glucosinolates in Pickling Cruciferous Vegetables." Journal of Agricultural and Food Chemistry 54.25 (2006): 9430-436. 7 pages.
TEACH Chemical Summary. Feb. 27, 2009. Benzene. 14 pages.
Telang, U., D. A. Brazeau, and M. E. Morris. "Comparison of the Effects of Phenethyl Isothiocyanate and Sulforaphane on Gene

(56) References Cited

OTHER PUBLICATIONS

Expression in Breast Cancer and Normal Mammary Epithelial Cells." Experimental Biology and Medicine 234.3 (2009): 287-95. 14 pages.

Textor, Susanne, and Jonathan Gershenzon. "Herbivore Induction of the Glucosinolate-myrosinase Defense System: Major Trends, Biochemical Bases and Ecological Significance." Phytochemistry Reviews 8.1 (2009): 149-70. 22 pages.

Theuwissen, E., E. Smit, and C. Vermeer. "The Role of Vitamin K in Soft-Tissue Calcification." Advances in Nutrition: An International Review Journal 3.2 (2012): 166-73. 8 pages.

Thimmulappa, Rajesh, et al. "Identification of Nrf2-regulated Genes Induced by the Chemopreventive Agent Sulforaphane by Oligonucleotide Microarray." Cancer Research 62 (2002): 5196-203. 9 pages.

Tobias, Mohn, et al. Supporting Information To: Seasonal Changes and Effect of Harvest on Glucosinolates in Isatis Leaves. 7 pages, 2008.

Tsao, Rong, Qing Yu, Irene Friesen, John Potter, and Mikio Chiba. "Factors Affecting the Dissolution and Degradation of Oriental Mustard-Derived Sinigrin and Allyl Isothiocyanate in Aqueous Media." Journal of Agricultural and Food Chemistry 48.5 (2000): 1898-902. 5 pages.

Tsugawa, Naoko. "Vitamin K Status of Healthy Japanese Women: Age-related Vitamin K Requirement for -carboxylation of Osteocalcin." The American Journal of Clinical Nutrition 83 (2006): 380-86. 7 pages.

Varghese, L. "Silibinin Efficacy against Human Hepatocellular Carcinoma." Clinical Cancer Research 11.23 (2005): 8441-448. 9 pages.

Vasanthi, Hannah R., Subhendu Mukherjee, and Dipak K. Das. "Potential Health Benefits of Broccoli—A Chemico-Biological Overview." Mini Reviews in Medicinal Chemistry 9.6 (2009): 749-59. 11 pages.

Verhoeven, Dorette T.h., et al. "A Review of Mechanisms Underlying Anticarcinogenicity by Brassica Vegetables." Chemico-Biological Interactions 103.2 (1997): 79-129. 51 pages.

Vig, Adarsh Pal, Geetanjali Rampal, Tarunpreet Singh Thind, and Saroj Arora. "Bio-protective Effects of Glucosinolates—A Review." LWT—Food Science and Technology 42.10 (2009): 1561-572. 12 pages.

Vissers, Linda, et al. "Intake of Dietary Phylloquinone and Menaquinones and Risk of Stroke." Journal of the American Heart Association: 1-8. 8 pages, 2013.

Volkel, W, et al. Abstract of "Toxicokinetics and biotransformation of 3-(4-methylbenzylidene)camphor in rats after oral administration." Toxicol. Appl. Pharmacol. 216(2006). 331-8. 1 page.

Volpe, S. L. "Magnesium in Disease Prevention and Overall Health." Advances in Nutrition: An International Review Journal 4.3 (2013): 378S-83S. 6 pages.

Wa, Ritschel, et al. "Abstract of Pharmacokinetics and Bioavailability of Beta-sitosterol in the Beagle Dog." 8 pages, 1990.

Wade, Kristina L., Ian J. Garrard, and Jed W. Fahey. "Improved Hydrophilic Interaction Chromatography Method for the Identification and Quantification of Glucosinolates." Journal of Chromatography A 1154.1-2 (2007): 469-72. 4 pages.

Wallin, Reidar, Leon Schurgers, and Nadeem Wajih. "Effects of the Blood Coagulation Vitamin K as an Inhibitor of Arterial Calcification." Thrombosis Research 122.3 (2008): 411-17. 14 pages.

Walters, D. G., et al."Cruciferous Vegetable Consumption Alters the Metabolism of the Dietary Carcinogen 2-amino-1-methyl-6-phenylimidazo[4,5-b]pyridine (PhIP) in Humans." Carcinogenesis 25.9 (2004): 1659-669. 11 pages.

Wan, Junxiang, and David Diaz-Sanchez. "Antioxidant Enzyme Induction: A New Protective Approach Against the Adverse Effects of Diesel Exhaust Particles." Inhalation Toxicology 19.S1 (2007): 177-82. 7 pages.

Wan, Junxiang, et al. "Phase II Enzymes Induction Blocks the Enhanced IgE Production in B Cells by Diesel Exhaust Particles." The Journal of Immunology 177 (2006): 3477-483. 8 pages.

Wang, Hu, et al. "Pharmacokinetics and Pharmacodynamics of Phase II Drug Metabolizing/Antioxidant Enzymes Gene Response by Anticancer Agent Sulforaphane in Rat Lymphocytes." Molecular Pharmaceutics 9.10 (2012): 2819-827. 20 pages.

Wang, Jingshu, et al. "Ursolic Acid Simultaneously Targets Multiple Signaling Pathways to Suppress Proliferation and Induce Apoptosis in Colon Cancer Cells." Ed. Chunhong Yan. PLoS ONE 8.5 (2013): E63872. 13 pages.

Wang, Min, et al. "Effects of Phytochemicals Sulforaphane on Uridine Diphosphate-Glucuronosyltransferase Expression as Well as Cell-Cycle Arrest and Apoptosis in Human Colon Cancer Caco-2 Cells." The Chinese Journal of Physiology (2012): 134-144. 11 pages.

Wang, Tianxin, Hao Liang, and Qipeng Yuan. "Optimization of Ultrasonic-stimulated Solvent Extraction of Sinigrin from Indian Mustard Seed (Brassica Juncea L.) Using Response Surface Methodology." Phytochemical Analysis 22.3 (2011): 205-13. 9 pages.

Weingarten, Hemi. "Sodium Benzoate—Extends Shelf Life, Shortens Yours." Fooducate. Fooducate, Sep. 4, 2014. 5 pages.

Williams, David J., et al. "Epithiospecifier Protein Activity in Broccoli: The Link between Terminal Alkenyl Glucosinolates and Sulphoraphane Nitrile." Phytochemistry 69.16 (2008): 2765-773. 9 pages.

World Health Organization. 2010. Preventing Disease Through Healthy Environments: Exposure to Benzene: A Major Public Health Concern. 5 pages.

Wu, Huahua, et al. "Preparation and Stability Investigation of the Inclusion Complex of Sulforaphane with Hydroxypropyl-β-cyclodextrin." Carbohydrate Polymers 82.3 (2010): 613-17. 5 pages.

Wu, L. "Dietary Approach to Attenuate Oxidative Stress, Hypertension, and Inflammation in the Cardiovascular System." Proceedings of the National Academy of Sciences 101.18 (2004): 7094-099. 6 pages.

Wu, Xiang, Qing-Hua Zhou, and Ke Xu. "Are Isothiocyanates Potential Anti-cancer Drugs?" Acta Pharmacologica Sinica 30.5 (2009): 501-12. 12 pages.

Wu, Yue, et al. "Inhibiting the TLR4-MyD88 Signalling Cascade by Genetic or Pharmacologic Strategies Reduces Acute Alcohol Dose-induced Sedation and Motor Impairment in Mice." British Journal of Pharmacology. 39 pages.

Xu, Changjiang, et al. "Suppression of NF-?B and NF-?B-regulated Gene Expression by Sulforaphane and PEITC through I?Ba, IKK Pathway in Human Prostate Cancer PC-3 Cells." Oncogene 24 (2005): 4486-495. 10 pages.

Xu, X., C. Pan, L. Zhang, and H. Ashida. "Immunomodulatory -Glucan from Lentinus Edodes Activates Mitogen-activated Protein Kinases and Nuclear Factor-B in Murine RAW 264.7 Macrophages." Journal of Biological Chemistry 286.36 (2011): 31194-1198. 5 pages.

Yadav, Vivek R., et al. "Targeting Inflammatory Pathways by Triterpenoids for Prevention and Treatment of Cancer." Toxins 2.10 (2010): 2428-466. 39 pages.

Yanaka, A., et al. "Dietary Sulforaphane-Rich Broccoli Sprouts Reduce Colonization and Attenuate Gastritis in Helicobacter Pylori-Infected Mice and Humans." Cancer Prevention Research 2.4 (2009): 353-60. 9 pages.

Yang, Bo, and Carlos F. Quiros. "Survey of Glucosinolate Variation in Leaves of Brassica Rapa Crops." Genetic Resources and Crop Evolution 57.7 (2010): 1079-089. 11 pages.

Yao, Jiayin, Min Zhi, and Chen Minhu. "Effect of Silybin on High-fat-induced Fatty Liver in Rats." Brazilian Journal of Medical and Biological Research 44.7 (2011): 652-59. 9 pages.

Ye, Lingxiang, et al."Quantitative Determination of Dithiocarbamates in Human Plasma, Serum, Erythrocytes and Urine: Pharmacokinetics of Broccoli Sprout Isothiocyanates in Humans." Clinica Chimica Acta 316.1-2 (2002): 43-53. 11 pages.

Yf, Jiang, et al. "Recurrence or Metastasis of HCC: Predictors, Early Detection and Experimental Antiangiogenic Therapy." World Journal of Gastroenterology 6.1 (2000): 61-65. 5 pages.

Yoshida, Minoru, et al. "Pharmacokinetics, Biological Effects, and Distribution of (1>3)-b-D-glucan in Blood and Organs in Rabbits." Mediators of Inflammation 6 (1997): 279-83. 5 pages.

(56) References Cited

OTHER PUBLICATIONS

Zhang, Qingzhi, Tomas Lebl, Agnieszka Kulczynska, and Nigel P. Botting. "The Synthesis of Novel Hexa-13C-labelled Glucosinolates from [13C6]-d-glucose." Tetrahedron 65.25 (2009): 4871-876. 6 pages.

Zhang, Y. "Anticarcinogenic Activities of Sulforaphane and Structurally Related Synthetic Norbornyl Isothiocyanates." Proceedings of the National Academy of Sciences 91.8 (1994): 3147-150. 4 pages.

Zhao, J., et al. "Tissue Distribution of Silibinin, the Major Active Constituent of Silymarin, in Mice and Its Association with Enhancement of Phase II Enzymes: Implications in Cancer Chemoprevention." Carcinogenesis 20.11 (1999): 2101-108. 8 pages.

Zhu, H., et al. "Antioxidants and Phase 2 Enzymes in Macrophages: Regulation by Nrf2 Signaling and Protection Against Oxidative and Electrophilic Stress." Experimental Biology and Medicine 233.4 (2008): 463-74. 13 pages.

Zhu, Jijiang, et al. "Detection of 2-Amino-1-Methyl-6-Phenylimidazo[4,5-b]-Pyridine-DNA Adducts in Normal Breast Tissues and Risk of Breast Cancer." Cancer Epidemiology, Biomarkers & Prevention 12 (2003): 830-37. 8 pages.

Zhu, Zhongling, et al. "A Phase I Pharmacokinetic Study of Ursolic Acid Nanoliposomes in Healthy Volunteers and Patients with Advanced Solid Tumors." International Journal of Nanomedicine 8 (2013): 129-36. 8 pages.

Masaru Ohtsuru, et al. The Interaction of L-Ascorbic Acid with the Active Center of Myrosinase. Biochimica et Biophysica Acta. (Apr. 1979) 384-391, vol. 567 No. 2. Elsevier/North-Holland Biomedical Press, Amsterdam, NL.

Yanyan Li, et al. Sulforaphane, a Dietary Component of Broccoli/Broccoli Sprouts, Inhibits Breast Cancer Stem Cells. Clinical Cancer Research May 2010 pp. 2580-2590 vol. 16 No. 9 (NIH Public Access Author Manuscript pp. 1-19).

I. Okic-Djordjevic, et al. GE132+Natural: Novel promising dietetic supplement with antiproliferative influence on prostate, colon and breast cancer cells. Journal of B.U.O.N. Official Journal of the Balkan Union of Oncology Apr. 2013: pp. 504-510. vol. 8 No. 2.

Sunan Wang, et al. Synergistic, Additive, and Antagonistic Effects of Food Mixtures on Total Antioxidant Capacities. J. Agric. Food Chem. Feb. 2011, pp. 960-968 vol. 59 No. 3.

Negi et al., "Nrf2 and NF-KB Modulation by Sulforaphane Counteracts Multiple Manifestations of Diabetic Neuropathy in Rats and High Glucose-Induced Changes" Current Neurovascular Research, 2011, 8(4):1-12.

Zaidman et al. "Medicinal mushroom modulators of molecular targets as cancer therapeutics," Appl Microbiol Biotechnol, 2005; 67:453-468.

\* cited by examiner

COMPOSITIONS COMPRISING SULFORAPHANE OR A SULFORAPHANE PRECURSOR AND A MUSHROOM EXTRACT OR POWDER

CROSS-REFERENCE TO RELATED APPLICATIONS

This application is a continuation application of International Application No. PCT/US2013/049248, having international filing date of Jul. 3, 2013, which claims priority to U.S. Provisional Patent Application No. 61/668,328, filed Jul. 5, 2012; U.S. Provisional Patent Application No. 61/668,342, filed Jul. 5, 2012; U.S. Provisional Patent Application No. 61/668,386, filed Jul. 5, 2012; U.S. Provisional Patent Application No. 61/668,396, filed Jul. 5, 2012; U.S. Provisional Patent Application No. 61/668,364, filed Jul. 5, 2012; U.S. Provisional Patent Application No. 61/668,374, filed Jul. 5, 2012; and U.S. Provisional Patent Application No. 61/794,417, filed Mar. 15, 2013, the disclosure of each of which is hereby incorporated in its entirety by reference.

FIELD OF THE INVENTION

The present invention relates to the combination of a sulforaphane precursor, an enzyme capable of converting the sulforaphane precursor to sulforaphane, an enzyme potentiator, and a mushroom (preferably maitake, shiitake, or reishi mushroom) extract or powder. The present invention also relates to the combination of sulforaphane or a derivative thereof and a mushroom (preferably maitake, shiitake, or reishi mushroom) extract or powder. The present invention also relates to the combination of a broccoli extract or powder and a mushroom (preferably maitake, shiitake, or reishi mushroom) extract or powder. The present invention provides compositions and methods relating to these combinations.

BACKGROUND OF THE INVENTION

The use of natural products is becoming increasingly popular with humans and companion animals. Some of these natural products are being incorporated into dietary supplements and medical foods. There is a need in the art for supplements which are useful as chemoprotective and/or antioxidant agents. In addition, there is a need in the art for pharmaceutical compositions and dietary supplements which are useful for conditions and disorders associated with the breast.

Chemoprotection through the use of natural products is evolving as a safe, effective, inexpensive, easily accessible, and practical means to prevent or reduce the occurrence of many conditions affecting humans and domesticated animals. It is known that carcinogens which can damage cells at the molecular level are often ingested and inhaled as non-toxic precursors. These non-toxic precursors may then convert into carcinogenic substances in the body. Chemoprotective agents, such as natural substances which can activate detoxifying enzymes or their co-factors, can counteract and allow for the elimination or potentiate the other naturally existing defenses such as the immune system.

Some natural products have antioxidant activity. Oxidative stress plays a major role in aging, the progression of neurodegenerative diseases as well as physiological trauma, such as ischemia. Antioxidant agents can reduce or inhibit the oxidation of vital biomolecules and may play a role in treating, preventing, or reducing the occurrence of cancer, coronary heart disease, stroke, and neurodegenerative diseases, Alzheimer's Disease, dementia, and stroke are examples of conditions affected by oxidative stress.

Cancers are largely thought to be a consequence of exposure to environmental challenges—whether from within (i.e.—estrogen, progesterone hormones) or externally (i.e.—bisphenol A (BPA) from plastic)—and chronic inflammation. Fortunately, the damage from environmental challenges can be negated via a complex network of Phase II chemoprotective enzymes found in many cell types of our body. It is well known that estrogens and their metabolites can lead to the proliferation of breast tissue and tumors. Worse, the quinone estrogen metabolites have the capacity to enter the breast tissue and migrate into the nucleus of ductal and glandular epithelial cells. There, they bind to DNA forming quinone estrogen DNA adducts which lead to downstream mutations. These mutations are thought to be responsible for the very foundation of a tumor: cancer initiation. Fortunately, a particular phase II enzyme, NAD(P)H:quinone oxidoreductase (NQO1) can take dangerous and highly reactive quinone estrogens and metabolize them to inert chemicals that can readily be removed from the body. Thus, a major mechanism to decrease cancer incidence is to induce protective Phase II enzymes including NQO1. Increased levels of NQO1 can be effective at treating, preventing, repairing, reducing the occurrence of, decreasing the symptoms associated with any conditions which are resulting from high levels of quinone estrogens. Examples of quinone estrogens include, but are not limited to catechol quinones of estrogen. Quinone estrogens are described in the following references, each of which is incorporated by reference in its entirety: Nutter et al. *Chem Res Toxicol,* 1994, 7:23-28; Cavalieri et al. *Ann N Y Acad Sci,* 2006; 1089:286-301; Bolton et al. *Chem Res Toxicol,* 2008, 21(1):93-101; and Cavalieri et al., *Biochimica et Biophysica Acta,* 2006, 1766:63-78.

An example of a natural product thought to have chemoprotective and antioxidant properties is sulforaphane. Sulforaphane is an organosulfur compound which is also known as 1-isothiocyanato-4-methylsulfinylbutane. The sulforaphane precursor, glucoraphanin, can be obtained from vegetables of the Brassicaceae family, such as broccoli, brussels sprouts, and cabbage. However, copious amounts of vegetables must be consumed in order to obtain levels adequate for chemoprevention. Glucoraphanin is converted into sulforaphane by a thioglucosidase enzyme called myrosinase, which occurs in a variety of exogenous sources such as Brassicaceae vegetables and endogenously in the gut microflora. However, upon ingestion of glucoraphanin, not all animals are capable of achieving its conversion to sulforaphane, most likely due to variations in microflora populations and overall health. In addition, in acidic environments such as the stomach, glucoraphanin can be converted to inert metabolites. The active metabolite, sulforaphane induces nuclear erythroid-2-related factor (Nrf2) which, in turn, upregulates the production of Phase II detoxification enzymes and cytoprotective enzymes such as glutathione S-transferases, NAD(P)H:quinone oxidoreductase (NQO1), and heme-oxygenase-1 (HO-1). Sulforaphane has been thought to induce the production of these enzymes without significantly changing the synthesis of P-450 cytochrome enzymes. The upregulation of Phase II enzymes is thought to play a role in a variety of biological activities, including the protection of the brain from cytotoxicity, the protection of the liver from the toxic effects of fat accumulation, and the detoxification of a variety of other tissues.

Sulforaphane and its precursor glucoraphanin have been studied extensively. Shapiro at al. (*Nutrition and Cancer,* (2006), Vol. 55(1), pp. 53-62) discuss a clinical Phase I study determining the safety, tolerability, and metabolism of broccoli sprout glucosinolates and isothiocyanates. Shapiro et al. discuss a placebo-controlled, double-blind, randomized clinical study of sprout extracts containing either glucosinolates such as glucoraphanin or isothiocyanates such as sulforaphane in healthy human subjects. The study found that administration of these substances did not result in systematic, clinically significant, adverse effects. Ye et al., (*Clinica Chimica Acta,* 200, 316:43-53) discuss the pharmacokinetics of broccoli sprout isiothiocyanates in humans.

A number of mushrooms have been used or studied for their medicinal effects. These "medicinal mushrooms" are thought to have beneficial properties, such as antiviral, antimicrobial, anticancer, antihyperglycemic, and/or anti-inflammatory activity. Examples of medicinal mushrooms include maitake, shiitake, reishi, cremini, almond, chestnut, wood ear, cloud ear, porcini, ink cap, yarta gunbu, enokitake, shemeji, tiger milk, morel, bamboo, golden oyster, pink oyster, king oyster, hiratake, cauliflower, white jelly, golden jelly, matsutake, Mexican truffle, and straw mushrooms.

Maitake mushrooms (*Grifola frondosa*) are edible mushroom consumed widely as food and used in traditional medicine to enhance immune function and to treat cancer. Maitake mushrooms, which contain glucans, are thought to have beneficial properties, such as antitumor and immunomodulatory effects. There exist standardized extracts from maitake mushroom that contain as active ingredients glucans such as protein-bound beta-glucans. Beta 1,6-glucan, a protein bound polysaccharide, has been identified as an active constituent in maitake mushrooms. Maitake mushrooms have been demonstrated to have antitumor effects, inhibiting tumor metastasis in vitro. In one study, tumor regression or significant improvements in symptoms were observed in half of the subjects using maitake extract. In a study of postmenopausal breast cancer patients, oral administration of maitake extract was shown to have immunomodulatory effects.

Shiitake mushrooms (*Lentinula edodes*) are edible mushrooms native to East Asia. Shiitake mushrooms contain mycochemicals, which are postulated to have antiviral, antibiotic, anti-inflammatory, antihypertensive and anticarcinogenic effects. This is thought to be largely a result of glucans, both alpha and beta glucans. Some shiitake mushroom extracts have alpha glucan content greater than 40%. Additionally, lentinan (1,3 beta-D-glucan), a polysaccharide isolated from shiitake, has been well studied and is thought to play a role in shiitake's beneficial effects. It has been shown to have anticancer effects in colon cancer cells, which may be due to its ability to suppress cytochrome P450 1A enzymes that are known to metabolize pro-carcinogens to active forms. Lentin, the protein component, has strong antifungal properties and has been found to inhibit proliferation of leukemic cells and suppress the activity of human immunodeficiency virus-1 reverse transcriptase.

Reishi mushrooms (*Ganoderma lucidum*), also known as lingzki mushrooms, are edible mushrooms found in East Asia. Reishi mushrooms are thought to have anti-tumor, anti-cancer, immunomodulatory, and immunotherapeutic effects. Reishi mushrooms have a number of components which are thought to contribute to its activity, including glucan, such as beta-glucan, canthaxanthin, sterols, coumarin, ganoderic acid, and mannitol.

Baker's yeast (*Saccaromyces cerevisiae*) can be a source of glucans, in particular, beta-glucans. The active components of Baker's yeast can be extracted in a number of ways, such as the methods described in Bacon et al. Biochem J, 1969, 114(3): 557-567, U.S. Pat. No. 7,803,605; U.S. Pat. No. 5,702,719; and U.S. Pat. No. 8,323,644, each of which is incorporated by reference in its entirety.

Glucans are described in the following references, which are each incorporated by reference in its entirety: Vetvicka et al. *Endocr Metab Immun Disord Drug Targets,* 2009, 9(1): 67-75, and Vetvicka et al. *J Med Food,* 2008: 11(4): 615-622.

Zhang et al. (*Proc. Natl. Acad. Sci.*, (1994), Vol. 91, pp. 3147-3150) discusses a study in Sprague-Dawley rats to determine the anticarcinogenic activities of sulforaphane and structurally related synthetic norbornyl isiothiocyanates. The study determined that administration of sulforaphane was effective in blocking the formation of mammary tumors.

Cornblatt et al. (*Carcinogenesis*, (2007), Vol. 38(7): pp. 1485-1490) discusses a study in Sprague-Dawley rats to determine the effect of sulforaphane in chemoprevention in the breast. The study determined that oral administration of either sulforaphane resulted in a 3-fold increase in NAD(P)H:quinone oxidoreductase (NQO1) enzymatic activity and a 4-fold elevated immunostaining of the heme oxygenase-1 (HO-1) enzyme in the mammary epithelium.

Munday et al. (*Cancer Res*, (2008), Vol. 68(5): pp. 1593-1600) discusses a study regarding the effects of a freeze-dried aqueous extract of broccoli sprouts on bladder cancer development in rats. The study found that administration of the broccoli sprout extract resulted in a significant induction of glutathione S-transferase and NAD(P)H:quinone oxidoreductase 1 in the bladder, which are enzymes having protective activity against oxidants and carcinogens.

Fang et al. (*J Altern Complem Med*, (2006), Vol. 12(2): pp. 125-132) discloses a study determining the antiproliferative effect of an ethyl acetate fraction of shiitake mushrooms on human breast carcinoma cell lines (MDA-MB-453 and MCF-7), a human nonmalignant breast epithelial cell line (MCF-10F), and two myeloma cell lines (RPMI08226 and IM-9). The study found that the inhibition of growth of tumor cells by the components in shiitake mushrooms may result from the induction of apoptosis.

Kim et al. (*J Med Food*, (2007), Vol. 10(1): pp. 25-31) discloses a study investigating the activation of natural killer (NK) cells and anticancer effects of an exo-biopolymer from rice bran cultured from *Lentinus edodes*. The study found that the exo-biopolymer may be effective for preventing and/or treating cancer through natural killer cell activation.

Louie et al. (*BJUI*, (2009), Vol. 153(9): pp. 1215-1221) discusses the synergistic effect of the combination of interferon-α and maitake mushroom D-fraction (PDF), a bioactive mushroom extract on anticancer activity of interferon-α in bladder cancer T24 cells in vitro.

Masuda et al. (*Biol. Pharm. Bull.* (2008), Vol. 31(6): pp. 1104-1108) discusses a study assessing the anti-metastatic activity of a fraction of maitake mushrooms in a murine model of lung metastasis. The study found that the fraction inhibited tumor metastasis by activation of natural killer cells and antigen-presenting cells (APCs) and suppressing adhesion molecules such as ICAM-1, leading to the inhibition of tumor cell adhesion to vascular endothelial cells.

European Patent Application No. 2 213 280 discloses formulations comprising glucosinolates such as glucoraphanin, and myrosinase, wherein the formulation is encapsulated or coated.

All references cited herein are incorporated by reference in their entirety.

SUMMARY OF THE INVENTION

The present invention provides a composition comprising: (i) a sulforaphane precursor, preferably glucoraphanin; (ii) an enzyme capable of converting the sulforaphane precursor to sulforaphane, preferably a glucosidase enzyme, more preferably a thioglucosidase enzyme, and most preferably myrosinase; (iii) an enzyme potentiator, preferably ascorbic acid; and (iv) a mushroom (preferably maitake, shiitake, or reishi mushroom) extract or powder. The present invention also provides a method of treating, preventing, reducing the occurrence of, decreasing the symptoms associated with, and/or reducing secondary recurrences of, cancer, in particular breast cancer, prostate cancer, colon cancer, lung cancer, and bladder cancer in a subject, comprising administering to the subject: (i) a sulforaphane precursor, (ii) an enzyme capable of converting the sulforaphane precursor to sulforaphane, (iii) an enzyme potentiator, and (iv) a mushroom (preferably maitake, shiitake, or reishi mushroom) extract or powder. The present invention also provides a method of increasing levels or increasing gene expression of NAD(P)H:quinone oxidoreductase 1 (NQO-1) in a subject, comprising administering to the subject: (i) a sulforaphane precursor, (ii) an enzyme capable of converting the sulforaphane precursor to sulforaphane, (iii) an enzyme potentiator, and (iv) a mushroom (preferably maitake, shiitake, or reishi mushroom) extract or powder. The present invention also provides a method of treating, preventing, reducing the occurrence of, decreasing the symptoms associated with, and/or reducing secondary recurrences of a disease or condition associated with elevated levels of quinone estrogen, comprising administering to the subject: (i) a sulforaphane precursor, (ii) an enzyme capable of converting the sulforaphane precursor to sulforaphane, (iii) an enzyme potentiator, and (iv) a mushroom (preferably maitake, shiitake, or reishi mushroom) extract or powder.

The present invention provides a composition comprising: (i) sulforaphane or a derivative thereof, and (ii) a mushroom (preferably maitake, shiitake, or reishi mushroom) extract or powder. The present invention also provides a method of treating, preventing, reducing the occurrence of, decreasing the symptoms associated with, and/or reducing secondary recurrences of, cancer, in particular breast cancer, prostate cancer, colon cancer, lung cancer, and bladder cancer in a subject, comprising administering to the subject: (i) sulforaphane or a derivative thereof, and (ii) a mushroom (preferably maitake, shiitake, or reishi mushroom) extract or powder. The present invention also provides a method of increasing levels or increasing gene expression of NAD(P)H:quinone oxidoreductase 1 (NQO-1) in a subject, comprising administering to the subject: (i) sulforaphane or a derivative thereof, and (ii) a mushroom (preferably maitake, shiitake, or reishi mushroom extract) or powder. The present invention also provides a method of treating, preventing, reducing the occurrence of, decreasing the symptoms associated with, and/or reducing secondary recurrences of a disease or condition associated with elevated levels of quinone estrogen, comprising administering to the subject: (i) sulforaphane or a derivative thereof, and (ii) a mushroom (preferably maitake, shiitake, or reishi mushroom) extract or powder.

The present invention provides a composition comprising: (i) a broccoli extract or powder, and (ii) a mushroom (preferably maitake, shiitake, or reishi mushroom) extract or powder. The present invention also provides a method of treating, preventing, reducing the occurrence of, decreasing the symptoms associated with, and/or reducing secondary recurrences of, cancer, in particular breast cancer, prostate cancer, colon cancer, lung cancer, and bladder cancer in a subject, comprising administering to the subject: (i) a broccoli extract or powder, and (ii) a mushroom (preferably maitake, shiitake, or reishi mushroom) extract or powder. The present invention also provides a method of increasing levels or increasing gene expression of NAD(P)H:quinone oxidoreductase 1 (NQO-1) in a subject, comprising administering to the subject, comprising administering to the subject: (i) a broccoli extract or powder, and (ii) a mushroom (preferably maitake, shiitake, or reishi mushroom) extract or powder. The present invention also provides a method of treating, preventing, reducing the occurrence of, decreasing the symptoms associated with, and/or reducing secondary recurrences of a disease or condition associated with elevated levels of quinone estrogen, comprising administering to the subject: (i) a broccoli extract or powder, and (ii) a mushroom (preferably maitake, shiitake, or reishi mushroom) extract or powder.

DETAILED DESCRIPTION OF THE INVENTION

Figure 1:
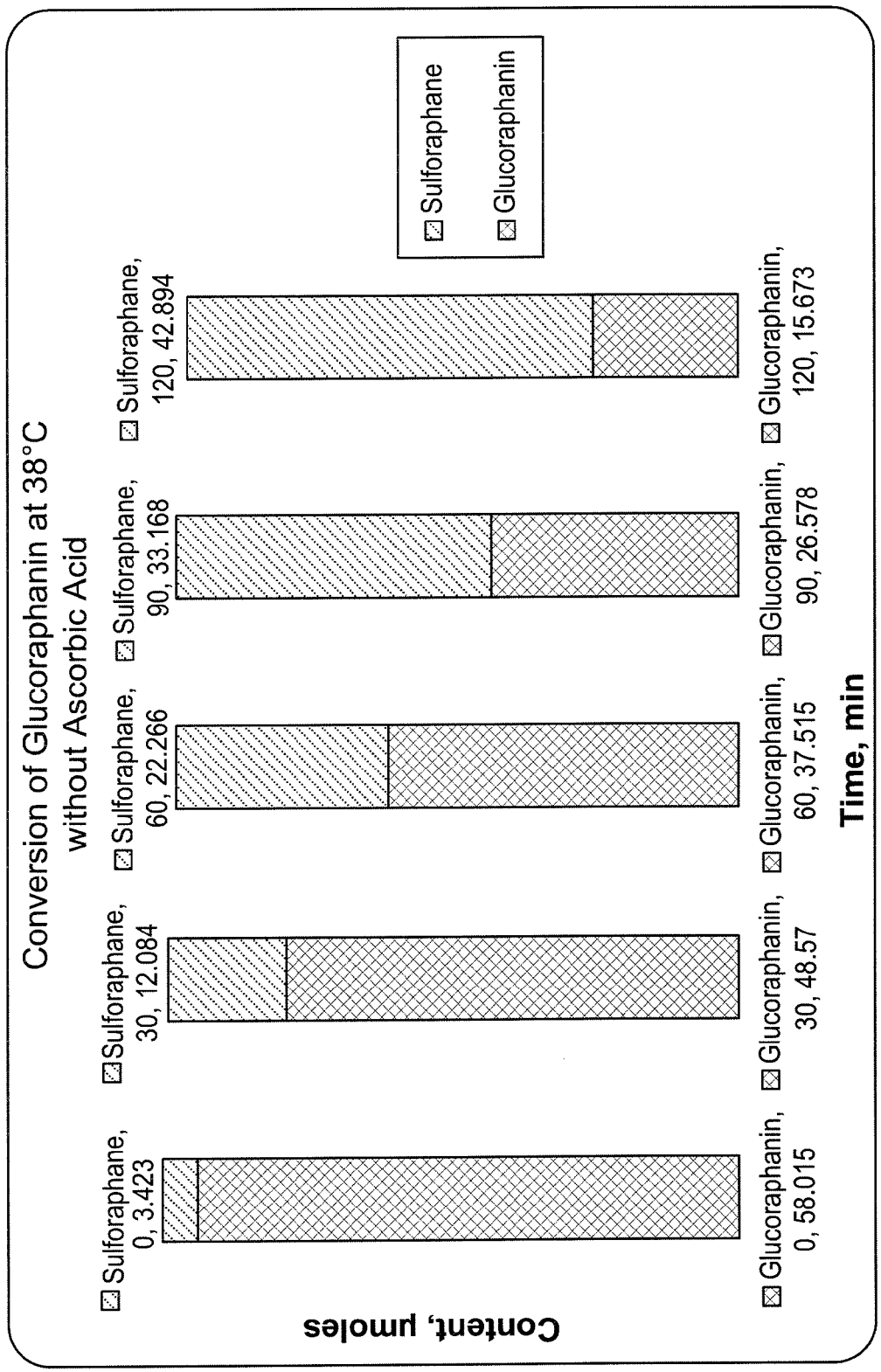
FIG. 1 is a graph showing the conversion of glucoraphanin at 38° C. without ascorbic acid, as described in Example 4.
Figure 2:
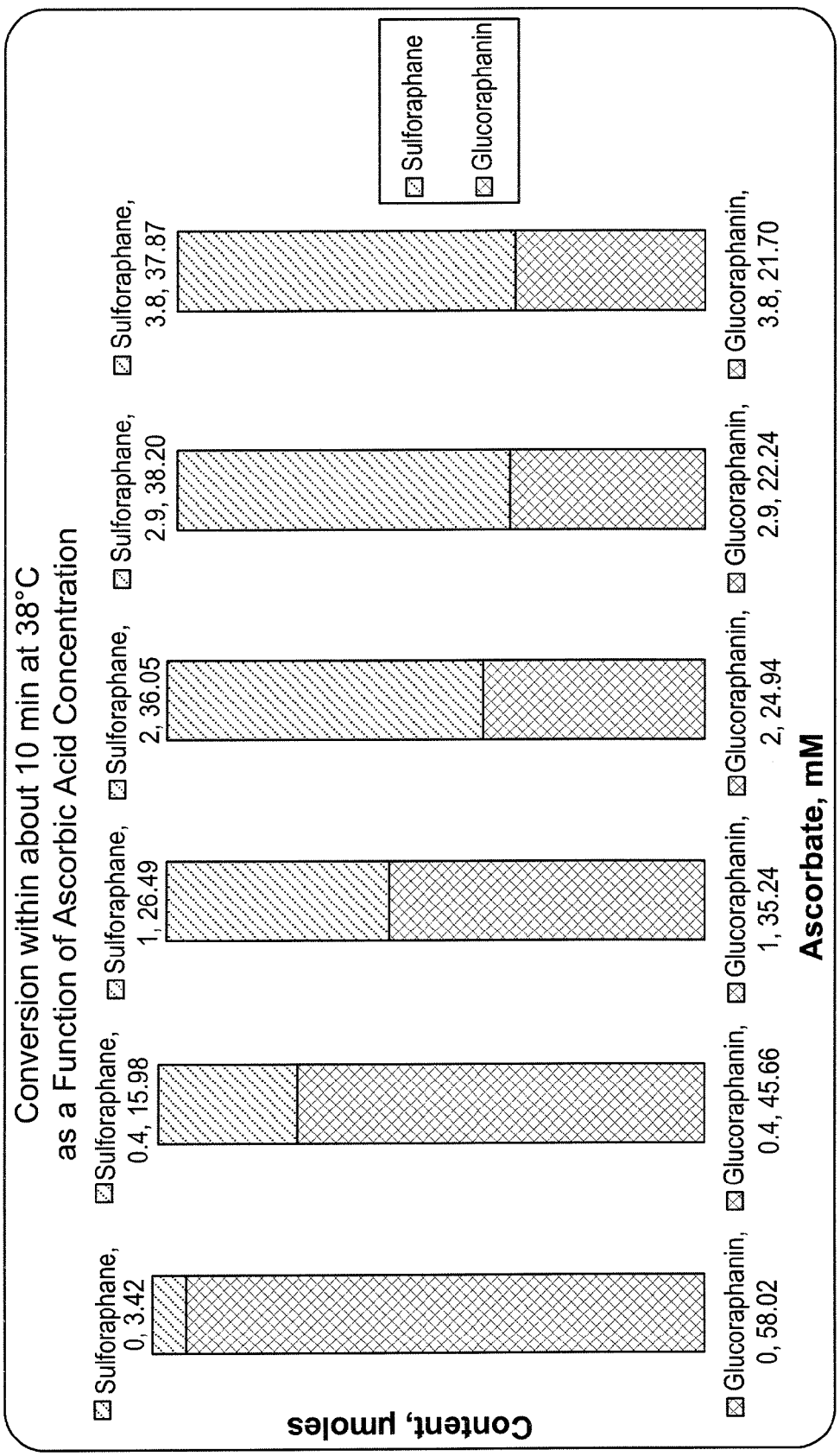
FIG. 2 is a graph showing the conversion within about 10 minutes at 38° C. as a function of ascorbic acid concentration, as described in Example 4.
Figure 3:
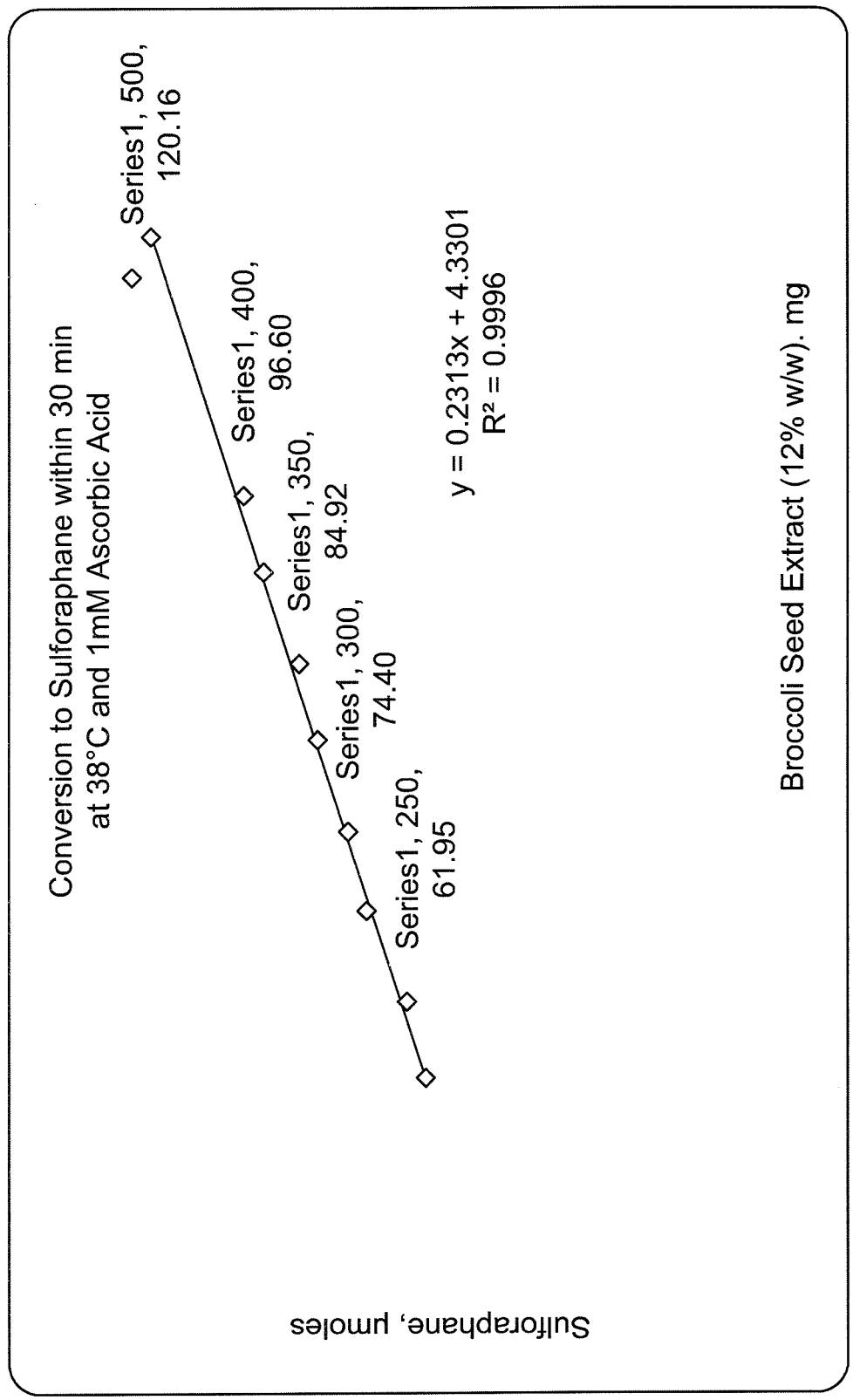
FIG. 3 is a graph showing the conversion to sulforaphane within 30 minutes at 38° C. and 1 mM ascorbic acid, as described in Example 4.

The present invention relates to the combination of a sulforaphane precursor, an enzyme capable of converting the sulforaphane precursor to sulforaphane, an enzyme potentiator, and a mushroom (such as maitake, shiitake, or reishi mushroom) extract or powder. The present invention also relates to the combination of sulforaphane or a derivative thereof and a mushroom (such as maitake, shiitake or reishi mushroom extract or powder. The present invention also relates to the combination of a broccoli extract or powder and a maitake, shiitake, or reishi mushroom extract or powder. The present invention also relates to the use of a mushroom extract or powder, with a mixture of one or more of the following: sulforaphane precursor, sulforaphane or a derivative thereof, and broccoli extract. The present invention provides compositions relating to these combinations.

The present invention also provides methods comprising administering these combinations. In some embodiments, the combination may be administered for treating, preventing, reducing the occurrence of, decreasing the symptoms associated with, and/or reducing secondary recurrences of, cancer, in particular breast cancer, prostate cancer, colon cancer, lung cancer, and bladder cancer in a subject, comprising administering to the subject. In some embodiments, the combination may be administered for increasing levels or increasing gene expression of NAD(P)H:quinone oxidoreductase 1 (NQO-1) in a subject. In some embodiments, the combination may be administered for treating, preventing, reducing the occurrence of, decreasing the symptoms associated with, and/or reducing secondary recurrences of a disease or condition associated with elevated levels of quinone estrogen.

Sulforaphane is also known as 1-isothiocyanato-4-methylsulfinylbutane. Derivatives of sulforaphane include, but are not limited to sulfoxythiocarbamate analogues of sulforaphane, 6-methylsulfinylhexyl isothiocyanate (6-HITC), and compounds which comprise the structure of sulforaphane with different side chains and/or various lengths of spacers between the isothiocyanato and sulfoxide groups. Examples of derivatives of sulforaphane include those described in the following references, each of which is incorporated herein by reference: Hu et al., *Eur J Med Chem*, 2013, 64:529-539; Ahn et al., *Proc Natl Acad Sci USA*, 2010, 107(21):9590-9595; and Morimistu et al., *J. Biol. Chem.* 2002, 277:3456-3463, and Baird et al., *Arch Toxicol*, 2011, 85(4):241-272.

In some embodiments, the composition comprises sulforaphane or a derivative thereof, preferably sulforaphane, in an amount of about 1 µg to about 10 g, preferably about 3 µg to about 5 g, preferably about 5 µg to about 1000 mg, preferably about 7 µg to about 750 mg, more preferably about 10 µg to about 500 mg, and most preferably about 100 µg to about 100 mg. In some embodiments, compositions suitable for human use comprise about 1 mg to about 20 mg.

In some embodiments, the methods of the present invention comprise administration of sulforaphane or a derivative thereof to a subject, preferably sulforaphane, in an amount of about 1 µg to about 10 g, preferably about 3 µg to about 5 g, preferably about 5 µg to about 1000 mg, preferably about 7 µg to about 750 mg, more preferably about 10 µg to about 500 mg, and most preferably about 100 µg to about 100 mg. In some embodiments wherein the subject is human, the method comprises administration of about 1 mg to about 20 mg. In some embodiments, the methods of the present invention comprise administration of sulforaphane or a derivative thereof to a subject, preferably sulforaphane, in an amount of about 0.01 µg/kg to about 0.2 g/kg, preferably about 0.05 µg/kg to about 0.07 g/kg, more preferably about 0.07 µg/kg to about 15 mg/kg, more preferably about 0.1 µg/kg to about 11 mg/kg, and most preferably about 0.2 µg/kg to about 7 mg/kg. In some embodiments wherein the subject is human, the method comprises administration of about 2 µg/kg to about 2 mg/kg, and more preferably about 0.01 mg/kg to about 0.3 mg/kg. The above amounts may refer to each dosage administration or a total daily dosage. The total daily dosage refers to the total amount of a compound or ingredient which is administered to a subject in a twenty-four hour period.

In some embodiments, the method comprises administration of more than one of a sulforaphane or a derivative thereof. In some embodiments, the compositions comprise more than one of a sulforaphane or a derivative thereof. For example, the methods or composition may comprise both sulforaphane and one or more derivatives thereof, or two or more derivatives. In some embodiments wherein the method or composition comprise more than one of a sulforaphane or a derivative thereof, the above amounts may refer to the amount of each sulforaphane or a derivative thereof, or the total amount of the more than one sulforaphane or derivative thereof.

The term "sulforaphane precursor" refers to any compound, substance or material which can be used to produce sulforaphane. In preferred embodiments, the sulforaphane precursor comprises a compound which can be converted or metabolized to sulforaphane, preferably by an enzyme. In some preferred embodiments, the sulforaphane precursor comprises glucoraphanin. Glucoraphanin is a glucosinolate which is also known as 4-methylsulfinylbutyl glucosinolate and 1-S-[(1E)-5-(methylsulfinyl)-N-(sulfonatooxy)pentanimidoyl]-1-thio-β-D-glucopyranose.

In some embodiments, the composition comprises about 1 µg to about 10 g, preferably about 250 µg to about 5 g, more preferably about 500 µg to about 2000 mg, even more preferably about 1 mg to about 750 mg, even more preferably about 1.5 mg to about 250 mg, even more preferably about 2 mg to about 100 mg, and most preferably about 3 mg to about 75 mg of the sulforaphane precursor, preferably glucoraphanin. In some embodiments, compositions suitable for human use comprise about 3.5 mg to about 50 mg of the sulforaphane precursor, preferably glucoraphanin.

In some embodiments, the method comprises administering the sulforaphane precursor, preferably glucoraphanin to a subject, in an amount of about 1 µg to about 10 g, preferably about 250 µg to about 5 g, more preferably about 500 µg to about 2000 mg, even more preferably about 1 mg to about 750 mg, even more preferably about 1.5 mg to about 250 mg, even more preferably about 2 mg to about 100 mg, and most preferably about 3 mg to about 75 mg. In some embodiments wherein the subject is a human, the method comprises administration of about 3.5 mg to about 50 mg. In some embodiments, the method comprises administering an amount of sulforaphane precursor to a subject in an amount of about 1 µg/kg to about 1000 mg/kg, preferably about 5 µg/kg to about 500 mg/kg, more preferably about 7.5 µg/kg to about 100 mg/kg, even more preferably about 10 µg/kg to about 25 mg/kg, and most preferably about 25 µg/kg to about 10 mg/kg. In some embodiments wherein the subject is a human, the method comprises administration of about 50 µg/kg to about 800 µg/kg. The above amounts may refer to each dosage administration or a total daily dosage.

In some embodiments, the method comprises administration of more than one sulforaphane precursor. In some embodiments, the composition comprises more than sulforaphane precursor. In some embodiments wherein the method or composition comprises more than one sulforaphane precursor, the above amounts may refer to the amount of each sulforaphane precursor, or the total amount of the sulforaphane precursors.

The sulforaphane precursor may be converted or metabolized to sulforaphane. In some embodiments, the sulforaphane precursor is converted to sulforaphane by an enzyme. In some embodiments, the enzyme capable of converting the sulforaphane precursor to sulforaphane comprises a glucosidase enzyme, preferably a thioglucosidase enzyme, and more preferably myrosinase. Myrosinase is also known as thioglucoside glucohydrolase.

In some embodiments, the composition comprises the enzyme in an amount of about 1 µg to about 1 µg, preferably about 50 µg to about 500 ng, and most preferably about 1 ng to about 150 ng. In some embodiments, compositions suitable for human use comprise about 5 ng to about 75 ng of the enzyme.

In some embodiments, the method comprises administering the enzyme, preferably myrosinase, in an amount of about 1 µg to about 1 µg, preferably about 50 µg to about 500 ng, and most preferably about 1 ng to about 150 ng. In some embodiments wherein the subject is a human, the method comprises administration of about 5 ng to about 75 ng of the enzyme. In some embodiments, the method comprises administering the enzyme to a subject in an amount of about 0.02 µg/kg to about 0.02 ug/kg, preferably about 0.7 µg/kg to about 7 ng/kg, and most preferably about 0.02 ng/kg to about 2 ng/kg. In some preferred embodiments wherein the subject is a human, the method comprises administration of about 0.1 ng/kg to about 1 ng/kg. The above amounts may refer to each dosage administration or a total daily dosage.

In some embodiments, the method comprises administration of more than one enzyme capable of converting the sulforaphane precursor to sulforaphane. In some embodiments, the composition comprises more than one enzyme capable of converting the sulforaphane precursor to sulforaphane. In some embodiments wherein the methods or compositions comprise more than one enzyme, the above amounts may refer to the amount of each enzyme, or the total amount of the enzymes.

The present invention also provides for the use of a broccoli extract and/or powder, including but not limited to broccoli seed and sprout extracts and powders. The present invention provides methods of administration of broccoli extract and/or powder, and compositions comprising broccoli extract and/or powder. In some embodiments, the broccoli extract or powder is standardized to contain about 1% to about 75% w/w, more preferably about 2.5% to about 50%, even more preferably about 5% to about 25%, and most preferably about 10% to about 20% of a sulforaphane precursor, preferably glucoraphanin. Examples of broccoli extracts and powders include but are not limited to those described in U.S. Pat. Nos. 5,411,986; 5,725,895; 5,968,505; 5,968,567; 6,177,122; 6,242,018; 6,521,818; 7,303,770, and 8,124,135, each of which is incorporated by reference in its entirety. Powders of broccoli may be obtained, for example, by air drying, freeze drying, drum drying, spray drying, heat drying and/or partial vacuum drying broccoli, preferably broccoli sprouts. In some embodiments, the compositions and methods comprise use of about 1 µg to about 10 g, more preferably about 250 µg to about 5 g, even more preferably about 500 µg to about 1 g, preferably about 600 µg to about 500 mg, more preferably about 750 µg to about 400 mg, and most preferably about 1 mg to about 300 mg of the broccoli extract. In some embodiments, the broccoli extract or powder is present in a composition or administered to a subject in amounts sufficient to provide a sulforaphane precursor or sulforaphane in the amounts described above. In some embodiments, the composition may further comprise an enzyme potentiator, preferably ascorbic acid. In some embodiments, the method may further comprise administration of an enzyme potentiator, preferably ascorbic acid.

The sulforaphane or a derivative thereof, the sulforaphane precursor, and/or the enzyme capable of converting the sulforaphane precursor to sulforaphane may be obtained from any source, including but not limited to one or more plants from the Brassicaceae (also known as Cruciferae) family. Examples of plants from the Brassicaceae family include, but are not limited to, the following: broccoli, Brussels sprouts, cauliflower, cabbage, horseradish, parsnip, radish, wasabi, watercress, and white mustard. In some preferred embodiments, sulforaphane precursor, preferably glucoraphanin, and the enzyme, preferably myrosinase, are obtained from broccoli, broccoli sprouts, or broccoli seeds. The sulforaphane precursor and the enzyme may be obtained from the same source or from different sources. In some embodiments, both the sulforaphane precursor and the enzyme may be obtained from an extract or powder from these plants, preferably a broccoli seed or sprout extract or powder.

The present invention provides for the use of an enzyme potentiator. Enzyme potentiators may be used to enhance the activity of the enzyme that is capable of converting the sulforaphane precursor to sulforaphane. In some embodiments, the enzyme potentiator comprises an enzyme co-factor, preferably ascorbic acid. Ascorbic acid, also known as ascorbate or vitamin C, can potentiate the activity of myrosinase. In some embodiments, without an enzyme potentiator such as ascorbic acid, the conversion reaction to sulforaphane may be too slow to occur in the location needed for peak absorption. The enzyme potentiator may be obtained from a natural source, or it may be produced synthetically.

In some embodiments, the compositions may comprise about 1 mg to about 500 mg, preferably about 1 mg to about 250 mg, and most preferably about 1 mg to about 125 mg of the enzyme potentiator. In some embodiments, compositions suitable for human use comprise about 1 mg to about 50 mg of the enzyme potentiator.

In some embodiments, the method of the present invention comprises administration of an enzyme potentiator, preferably ascorbic acid, in an amount of about 1 mg to about 500 mg, preferably 1 mg to about 250 mg, and most preferably about 1 mg to about 125 mg. In some embodiments wherein the subject is a human, the method comprises administration of about 1 mg to about 50 mg. In some embodiments, the method of the present invention comprises administration of the enzyme potentiator, preferably ascorbic acid, in an amount of about 0.01 mg/kg to about 3 mg/kg, and most about 0.02 mg/kg to about 2 mg/kg. In some embodiments wherein the subject is a human, the method comprises administration of about 0.02 mg/kg to about 0.7 mg/kg of the enzyme potentiator. The above amounts may refer to each dosage administration or a total daily dosage.

In some embodiments, the method comprises administration of more than one enzyme potentiator. In some embodiments, the composition comprises more than one an enzyme potentiator. In some embodiments wherein the method or composition comprises more than one enzyme potentiator, the above amounts may refer to the amount of each enzyme potentiator, or the total amount of the enzyme potentiators.

The present invention provides for the use of a mushroom extract or powder. In some embodiments, the mushrooms may comprise "medicinal mushrooms," including, but not limited to maitake, shiitake, reishi, cremini, almond, chestnut, wood ear, cloud ear, porcini, ink cap, yarta gunbu, enokitake, shemeji, tiger milk, morel, bamboo, golden oyster, pink oyster, king oyster, hiratake, cauliflower, white jelly, golden jelly, matsutake, Mexican truffle, and straw mushrooms. In preferred embodiments, the mushroom comprises maitake mushroom, shiitake mushroom, reishi mushroom, and/or a mixture of one or more of these.

Maitake mushroom belongs to the species *Grifola frondosa*. Maitake mushroom may contain a number of fractions having biological activity. Examples of components found in maitake mushroom include, but are not limited to: glucans (such as alpha-glucans and beta-glucans); lipids (such as octadecanoic and octadecadienoic acids); phospholipids (such as phosphatidylethanolamine, phosphatidylcholine, phosphatidylinositol, phosphatidylserine and phosphatidic acid).

Shiitake mushroom belongs to the species *Lentinula edodes*. Shiitake mushroom may contain a number of fractions having biological activity. Examples of components found in shiitake mushrooms include, but are not limited to, glucans (such as alpha-glucans and beta-glucans), proteins (such as lentin); lipids (such as linoleic acid); and lignins.

Reishi mushrooms belong to the species *Ganoderma lucidum*. Reishi mushrooms may contain a number of fractions having biological activity. Examples of components found in reishi mushroom include, but are not limited to: glucan (such as alpha-glucans and beta-glucans), canthaxanthin, sterols, coumarin, ganoderic acid, and mannitol.

In some preferred embodiments, the mushroom extract or powder comprises one or more glucans. A glucan is a polysaccharide of a D-glucose monomer linked by glycosidic bonds and may be in the alpha or beta form. In some embodiments, the glucan comprises one or more alpha-glucan and/or beta-glucans. Alpha-glucans include, but are not limited to, 1,4-α-glucans and 1,6-α-glucans and beta-glucans include, but are not limited to, 1,3-β-glucans, 1,4-β-glucans, and 1,6-β-glucans. The glucans may be expressed in a variety of polymeric configurations. In preferred embodiments, the maitake mushroom extract or powder comprises 1,3-β-glucans and/or 1,6-β-glucans. In preferred embodiments, the shiitake mushroom extract or powder comprises 1,4-α-glucans. In preferred embodiments, the reishi mushroom extract or powder comprises 1,3-β-glucans and/or 1,6-β-glucans. In some embodiments, the compositions and methods of the present invention may comprise use of glucans in a purified form or glucans produced synthetically, instead of a mushroom extract or powder.

In some embodiments, a maitake mushroom extract or powder may be used. In some embodiments, the maitake mushroom extract or powder is standardized to contain about 1% to about 75%, more preferably about 5% to about 50%, even more preferably about 10% to about 30%, and most preferably about 15% to about 20% of one or more glucans, preferably beta-glucans, and more preferably 1,3-beta glucan and/or 1,6-beta-glucan. Examples of maitake mushroom extracts and powders include, but are not limited to, those described in U.S. Pat. No. 5,854,404; WO 2007142130, EP 0893449; WO2009063885; WO2006107208; WO2007024496; and WO2001054673, each of which is incorporated by reference in its entirety. Powders of maitake mushroom may be obtained, for example, by air drying, freeze drying, drum drying, spray drying, heat drying and/or partial vacuum drying maitake mushrooms. In some embodiments, the composition comprises about 250 µg to about 100 mg, preferably about 500 µg to about 75 mg, and most preferably about 750 µg to about 50 mg. In some embodiments, compositions suitable for humans comprise about 1 mg to about 20 mg of maitake mushroom extract. In some embodiments, the method comprises administration of about 250 µg to about 100 mg, preferably about 500 µg to about 75 mg, and most preferably about 750 µg to about 50 mg. In some embodiments wherein the subject is human, the method comprises administration of about 1 mg to about 20 mg of maitake mushroom extract. The above amounts may refer to each dosage administration or a total daily dosage.

In some embodiments, a shiitake mushroom extract or powder may be used. In some embodiments, the shiitake mushroom extract or powder is standardized to contain about 1% to about 75%, preferably about 10% to about 60%, even more preferably about 25% to about 50%, and most preferably about 30% to about 40% of one or more glucans, preferably alpha-glucans, and more preferably 1,4-alpha-glucan. Examples of shiitake mushroom extracts include, but are not limited to, those described in U.S. Pat. No. 5,780,097; U.S. Pat. No. 6,582,723; WO2005107496, WO2007024496, and WO2000033069, each of which is incorporated by reference in its entirety. Powders of maitake mushroom may be obtained, for example, by air drying, freeze drying, drum drying, spray drying, heat drying and/or partial vacuum drying maitake mushrooms. In some embodiments, the composition comprises about 1 mg to about 1 g, preferably about 10 mg to about 500 mg, and most preferably about 25 mg to about 300 mg. In some embodiments, compositions suitable for humans comprise about 50 mg to about 250 mg of shiitake mushroom extract or powder. In some embodiments, the method comprises administration of about 1 mg to about 1 g, preferably about 10 mg to about 500 mg, and most preferably about 25 mg to about 300 mg. In some preferred embodiments wherein the subject is human, the method comprises administration of about 50 mg to about 250 mg of shiitake mushroom extract or powder to a subject. The above amounts may refer to each dosage administration or a total daily dosage. The above amounts may refer to each dosage administration or a total daily dosage.

In some embodiments, a reishi mushroom extract or powder may be used. In some embodiments, the reishi mushroom extract comprises about 1% to about 75%, more preferably about 5% to about 50%, even more preferably about 10% to about 30%, and most preferably about 15% to about 20% of one or more glucans, preferably beta-glucans, and more preferably 1,3-beta glucan and/or 1,6-beta-glucan. Powders of maitake mushroom may be obtained, for example, by air drying, freeze drying, drum drying, spray drying, heat drying and/or partial vacuum drying maitake mushrooms.

In some embodiments, the composition and/or method comprises use of one type or mushroom extract or powder, such as maitake mushroom extract or powder, shiitake mushroom extract or powder or reishi mushroom extract or powder. In some embodiments, the composition and/or method comprises use of a mixture of one or more types of mushroom extract or powder. In some embodiments, the composition and/or method comprises use of a mixture of one or more of the following: maitake mushroom extract or powder, shiitake mushroom extract or powder, and reishi mushroom extract or powder. The composition and method may comprise use of an extract or a powder, or a mixture of extracts and powders.

The present invention also provides for the use of any glucan-rich component in place of, or in addition to, the mushroom extract or powder. An example of a glucan-rich component is Baker's yeast. In some embodiments, yeast preparations may be used. In some embodiments, the yeast preparation comprises about 0.1% to about 50%, preferably about 0.5% to about 25%, and most preferably about 0.5% to about 10% of one or more glucans. Examples of yeast preparations include those discussed in U.S. Pat. No. 5,223,491 and U.S. Pat. No. 5,576,015, each of which is incorporated by reference in its entirety.

The methods of the present invention may further comprise administration of one or more additional components. The compositions of the present invention may further comprise one or more additional components. The additional components may include active pharmaceutical ingredients, nutritional supplements, and nutritional extracts. Examples of additional components include, but are not limited, ursolic acid, quercetin or a derivative thereof, an aminosugar such as glucosamine, a glycosaminoglycan such as chondroitin, avocado/soybean unsaponifiables, vitamins such as vitamin K2, coffee fruit, magnesium, ursolic acid, proanthocyanidins, alpha- and beta-glucans, curcumin, phytosterols, phytostanols, and S-adenosylmethionine (SAMe). These additional components may be present in milk thistle (*Silybum marianum*) extract (silymarin), cranberry (*Vaccinium macrocarpon*) extract (proanthocyanidins, quercetin, and ursolic acid), turmeric (*Curcuma longa*).

In some embodiments, the ratio of beta-glucan to sulforaphane or a derivative of (beta-glucan:sulforaphane or a derivative of) is about 50:1 to about 1:50, preferably about 25:1 to about 1:25, more preferably about 10:1 to about 1:20, more preferably about 5:1 to about 1:10, even more preferably about 1:1 to about 1:8, and most preferably about 1:3 to about 1:5. In some embodiments, the ratio of alpha-glucan to sulforaphane or a derivative of (alpha-glucan:sulforaphane or a derivative of) is about 1:50 to about 50:1, preferably about 1:10 to about 25:1, more preferably about 1:5 to about 20:1, more preferably about 1:1 to about 15:1, even more preferably about 2:1 to about 10:1, and most preferably about 3:1 to about 8:1. In some embodiments, the ratio of beta-glucan to sulforaphane precursor of (beta-glucan:sulforaphane precursor) is about 50:1 to about 1:50, preferably about 30:1 to about 1:35, more preferably about 20:1 to about 1:25, more preferably about 10:1 to about 1:20, even more preferably about 5:1 to about 1:15, and most preferably about 1:1 to about 1:10. In some embodiments, the ratio of alpha-glucan to precursor (alpha-glucan:precursor) is about 1:50 to about 100:1, preferably about 1:25 to about 75:1, more preferably about 1:10 to about 50:1, more preferably about 1:5 to about 40:1, even more preferably about 1:1 to about 30:1, and most preferably about 2:1 to about 20:1

In some embodiments, the composition comprises a unit dosage form, including but not limited to pharmaceutical dosage forms suitable for oral, rectal, intravenous, subcutaneous, intramuscular, transdermal, transmucosal, and topical. In some preferred embodiments, the composition comprises an orally administrable dosage form or a rectally administrable dosage form. Examples of orally administrable dosage forms include, but are not limited to a tablet, capsule, powder that can be dispersed in a beverage, a liquid such as a solution, suspension, or emulsion, a soft gel/chew capsule, a chewable bar, or other convenient dosage form known in the art. In preferred embodiments, the composition comprises a tablet, capsule, or soft chewable treat. The orally administrable dosage forms may be formulated for immediate release, extended release or delayed release.

In some embodiments, at least the sulforaphane precursor, the enzyme, and the enzyme potentiator are provided in a dosage form which allows for the release in an area of the gastrointestinal tract having a pH of at least 4 and preferably at least 5, such as the small intestine, preferably the duodenum. In some embodiments, at least the sulforaphane or derivative thereof and/or the broccoli extract or powder are provided in a dosage form which allows for the release in an area of the gastrointestinal tract having a pH of at least 4 and preferably at least 5, such as the small intestine, preferably the duodenum. In some embodiments, the mushroom extract or powder and/or any optional additional components are also released in an area of the gastrointestinal tract having a pH of at least 4 and preferably at least 5, such as the small intestine, preferably the duodenum. The small intestine includes the duodenum, jejunum, and ileum.

In some embodiments, each of these components (i.e, sulforaphane precursor, enzyme, enzyme potentiator, sulforaphane or a derivative thereof, broccoli extract or powder, mushroom extract or powder, and/or additional components) are released simultaneously or concomitantly (i.e., within a short period of time of each other). This provides benefits over glucoraphanin-containing compositions formulated to release the glucoraphanin in an area of the gastrointestinal tract having a pH below 4, such as the stomach. In low pH environments such as this, the acidic environment may divert conversion of sulforaphane precursor to other, physiologically inactive end products, such as sulforaphane nitrile and epithionitrile.

In some embodiments, the compositions may comprise orally administrable compositions which comprise enteric coated dosage forms or any dosage form which is resistant to degradation in an area of the gastrointestinal tract having pH below 4, such as the stomach. For example, the orally administrable composition may comprise a tablet or capsule comprising an enteric coating. The enteric coating may comprise materials including, but not limited to cellulose acetate phthalate, hydroxypropyl methylcellulose phthalate, polyvinyl acetate phthalate, methacrylic acid copolymer, methacrylic acid:acrylic ester copolymer, hydroxypropyl methylcellulose acetate succinate, hydroxypropyl methylcellulose trimellitate, shellac, cellulose acetate trimellitate, carboxymethylethylcellulose, and mixtures thereof. The enteric coating may comprise any suitable enteric polymers known in the art. In some embodiments, one or more of the components in the composition may be embedded in a matrix of enteric polymers. In some embodiments, the orally administrable compositions comprise a capsule that dissolves slowly in gastric acid and travels to the small intestine, such as DRCAPS™ acid resistant capsules, which are marketed by CAPSUGEL® or any other acid resistant capsules.

In the most preferred form, the orally administrable composition is surrounded by a coating that does not dissolve unless the surrounding medium is at a pH of at least 4, and more preferably at least 5. Alternatively, a coating may be employed which controls the release by time, as opposed to pH, with the rate adjusted so that the components are not released until after the pH of the gastrointestinal tract has risen to at least 4, and more preferably at least 5. Thus, a time-release formulation may be used to prevent gastric presence of the sulforaphane precursor, the enzyme capable of converting the sulforaphane precursor to sulforaphane, and the enzyme potentiator, or of the sulforaphane. The coating layer(s) may be applied onto orally administrable composition using standard coating techniques. The enteric coating materials may be dissolved or dispersed in organic or aqueous solvents. The pH at which the enteric coat will dissolve can be controlled by a polymer, or combination of polymers, selected and/or ratio of pendant groups. For example, dissolution characteristics of the polymer film can be altered by the ratio of free carboxyl groups to ester groups. Enteric coating layers also contain pharmaceutically acceptable plasticizers such as triethyl citrate, dibutyl phthalate, triacetin, polyethylene glycols, polysorbates or other plasticizers. Additives such as dispersants, colorants, anti-adhering and anti-foaming agents may also be included.

The compositions may contain one or more non-active pharmaceutical ingredients (also known generally as "excipients"). Non-active ingredients, for example, serve to solubilize, suspend, thicken, dilute, emulsify, stabilize, preserve, protect, color, flavor, and fashion the active ingredients into an applicable and efficacious preparation that is safe, convenient, and otherwise acceptable for use. The excipients are preferably pharmaceutically acceptable excipients. Examples of classes of pharmaceutically acceptable excipients include lubricants, buffering agents, stabilizers, blowing agents, pigments, coloring agents, flavoring agents, fillers, bulking agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof.

In some embodiments, the combination of (i) a sulforaphane precursor, preferably glucoraphanin, (ii) an enzyme capable of converting the sulforaphane precursor to sulforaphane, preferably a glucosidase enzyme, more preferably a thioglucosidase enzyme, and most preferably myrosinase, (iii) an enzyme potentiator, preferably an enzyme cofactor, more preferably ascorbic acid, and (iv) a mushroom extract or powder (which contains glucans) demonstrates a synergistic effect. In some embodiments, the combination of sulforaphane (or a derivative thereof) and a mushroom extract or powder (which contains glucans) demonstrates a synergistic effect. Synergy refers to the effect wherein a combination of two or more components provides a result which is greater than the sum of the effects produced by the agents when used alone. In preferred embodiments, the synergistic effect is greater than an additive effect. In some embodiments, the combination of a sulforaphane precursor, an enzyme capable of converting the sulforaphane precursor to sulforaphane, an enzyme potentiator, and a maitake, shiitake, or reishi mushroom extract or powder has a statistically significant, greater effect compared to: (i) each component alone, (ii) the combination of sulforaphane precursor and the enzyme alone; and/or (iii) the combination of sulforaphane precursor, the enzyme, and the enzyme potentiator alone.

In preferred embodiments, the combination of the sulforaphane precursor, the enzyme, the enzyme potentiator, and a mushroom extract or powder (which contains glucans) demonstrates synergy by having a statistically significant and/or greater than additive effect compared to the sulforaphane precursor alone and the mushroom extract or powder alone. In some embodiments, the combination of glucoraphanin, myrosinase, ascorbic acid, and a mushroom extract or powder has a synergistic effect compared to the combination of glucoraphanin, myrosinase, ascorbic acid alone; and compared to glucans alone.

In some embodiments, the combination of a sulforaphane (or a derivative thereof) and a mushroom extract or powder has a statistically significant and/or greater than additive effect than: (i) sulforaphane (or a derivative thereof) alone, and/or (ii) a mushroom extract or powder alone. In some embodiments, the combination of sulforaphane and glucan has a synergistic effect compared to sulforaphane alone, and glucan alone.

In some embodiments, the combination of broccoli extract or powder and a mushroom extract or powder has a statistically significant and/or greater than additive effect than: (i) broccoli extract or powder alone, and/or (ii) a mushroom extract or powder alone. In some embodiments, the combination of broccoli extract or powder and glucan has a synergistic effect compared to broccoli extract or powder alone, and glucan alone.

The present invention provides methods of use, including methods of administration to a subject in need thereof. In some embodiments, the method comprises administration of the combination of a sulforaphane precursor, an enzyme capable of converting the sulforaphane precursor to sulforaphane, an enzyme potentiator, and a mushroom extract or powder. In some embodiments, the method comprises administration of the combination of a sulforaphane or a derivative thereof and a mushroom extract or powder. In some embodiments, the method comprises administration of the combination of a broccoli extract or powder and a mushroom extract or powder.

In some embodiments, the method relates to treating, preventing, reducing the occurrence of, decreasing the symptoms associated with, and/or reducing secondary recurrences of, cancer, in particular breast cancer, prostate cancer, colon cancer, lung cancer, liver cancer, and bladder cancer in a subject. The methods may be useful in reducing damage or slowing damage to tissues and organs, such as the breast, prostate, colon, lung, liver, and bladder. The present invention provides methods of treating, preventing, decreasing the symptoms associated with, and/or reducing secondary recurrences of diseases and conditions associated with the reproductive system (including but not limited to the breast and prostate), colon, liver, bladder, kidney, central nervous system, cardiovascular system, pulmonary system, genitourinary system, hematopoietic system, and joints. The present invention also provides for methods of treating, preventing, decreasing the symptoms associated with, and/or reducing secondary recurrences of cysts, such as benign cysts.

In some embodiments, the method relates to increasing levels or increasing gene expression of NAD(P)H:quinone oxidoreductase 1 (NQO-1) in a subject. The method may also be useful in treating, preventing, decreasing the symptoms associated with, and/or reducing secondary recurrences of diseases and conditions which would be benefited from an increase in gene expression or levels of NQO-1. Examples of such diseases and conditions include, but are not limited to cancer, myelodysplastic syndrome, cardiovascular disease, and tardive dyskinesia.

In some embodiments, the method relates to treating, preventing, reducing the occurrence of, decreasing the symptoms associated with, and/or reducing secondary recurrences of a disease or condition associated with elevated levels of quinone estrogen. Examples of such diseases or conditions include, but are not limited to Examples of such diseases and conditions include, but are not limited to cancer, myelodysplastic syndrome, cardiovascular disease, and tardive dyskinesia.

In some embodiments, the methods relate to providing a beneficial effect on biomarkers, and treating, preventing, reducing the occurrence of, decreasing the symptoms associated with abnormal levels of these biomarkers. Examples of such biomarkers include, but are not limited to NADPH-dependent enzymes, thioredoxin (TXN), thioredoxin reductase-1 (Txnrd-1), glutamate-cysteine ligase subunit (GCLC), sulfotransferase 1A1 (SULT1A1), heme oxygenase-1 (HMOX1), glutathione peroxidase-3 (GPx-3), glutathione S-transferse theta 2 (GSTT2), microsomal glutathione S-transferase 1 (MGST1), aldehyde oxidase (AOX1), aldo-keto reductase 1B8 (Akr1b8), flavin-containing monooxygenase 2 (FMO2), Fc receptor region receptor III (Fcgr3), tryptase beta 1 (TPSB1), mast cell protease-6 (Mcpt6), neurexin-1-alpha (NRXN-1), microphthalmia-associated transcription factor (MITF), type II iodothyronine deiodinase (DIO2), angiopoietin-14 (Angpt14), cluster of differentiation (CD36), and Nte1. Diseases or conditions associated with elevated or abnormal levels of these biomarkers include, but are not limited to cancer, pulmonary and central nervous system tuberculosis, multiple sclerosis, Crohn's disease, atherosclerosis, osteoarthritis, asthma, stroke, emphysema, diabetic nephropathy, chronic histiocytic intervillositis of the placenta, hypertension, abdominal aortic aneurysm, inflammatory bowel disease, chronic rhinosinusitis, coronary artery disease, and kidney disease.

In some embodiments, the method comprises administering to a subject in need thereof a combination of sulforaphane and a mushroom extract or powder containing glucan. In some embodiments the method comprises administering to a subject in need thereof a combination of broccoli extract or powder and a mushroom extract or powder containing glucan. In some preferred embodiments, the method comprises administering to the subject a combination of glucoraphanin, myrosinase, ascorbic acid, and a mushroom extract or powder containing glucan. In preferred embodiments, the combinations demonstrate a synergistic effect in the methods of the present invention.

In preferred embodiments, one or more components of the combinations (for example, the sulforaphane precursor, the enzyme capable of converting the sulforaphane precursor to sulforaphane, the enzyme potentiator, the mushroom extract or powder; or the sulforaphane or derivative thereof and the mushroom extract or powder; or the broccoli extract or powder and the mushroom extract or powder) are administered together in one composition or dosage form, or separately, preferably within a period in which their therapeutic properties overlap. In some embodiments, the components of the combinations may be administered in two or more orally administrable compositions or dosage forms. For example, in some embodiments, the sulforaphane precursor, the enzyme capable of converting the sulforaphane precursor to sulforaphane, and the enzyme potentiator are administered in one orally administrable dosage form, while the a mushroom extract or powder are administered in one or more separate or additional orally administrable dosage form(s). In preferred embodiments, the components of the combination are administered in one dosage form.

In some embodiments, the combination may be administered at a frequency of 1 to 10 times daily, preferably 1 to 5 times daily, more preferably 1 to 3 times daily, and most preferably 1 time daily.

The dosages disclosed in this application refer preferably to dosages suitable for humans. Dosage calculations can be determined by those of skilled in the art by evaluating body weight, surface area, metabolic rate, and species differences.

The term "subject" refers to any animal, including mammals and birds. Mammals include, but are not limited to, humans, dogs, cats, horses, cows, camels, elephants, lions, tigers, bears, seals, and rabbits. In preferred embodiments, the subjects comprise mammals that are not consumed as food, such as humans, cats, and dogs.

EXAMPLES

Example 1

Formulations

The following are exemplary formulation of the present invention:
Formulation A
Glucoraphanin-containing broccoli seed extract (about 12% w/w), 50 mg to 5 grams
Myrosinase-containing freeze-dried broccoli sprout powder, 25 mg to 500 mg
Ascorbic acid, 1 mg to 50 mg
Alpha Glucan-containing shiitake mushroom extract (about 40% w/w), 1 mg to 250 mg
Formulation B
Glucoraphanin-containing broccoli seed extract (about 12% w/w), 50 mg to 5 grams
Myrosinase-containing freeze-dried broccoli sprout powder, 25 mg to 500 mg
Ascorbic acid, 1 mg to 50 mg
Beta Glucan-containing maitake mushroom extract (about 20% w/w), 1 to 100 mg
Formulation C
An orally administrable composition comprising:
Broccoli seed extract
Broccoli sprout extract
Maitake mushroom extract
Ascorbic acid
Hydroxypropylmethyl cellulose
Microcrystalline cellulose
Corn starch
Ethylcellulose
Croscarmellose sodium
Sodium starch glycolate
Crospovidone
Silicon dioxide
Sodium alginate
Medium chain triglycerides
Maltodextrin
Oleic Acid
Magnesium stearate
Stearic acid Example 2

A Hydrophobic Interaction Chromatographic (HILIC) method was developed, comprising the following conditions:
Column: Waters BEH Amide, 1.7-µm particle size; 2.1 mm×100 mm
Mobile Phase: 20% 10 mM Ammonium Acetate, pH 5.0; 80% Acetonitrile;
Separation mode: isocratic
Column Temperature: 70° C.
Flow Rate: 0.7 mL/min
The above conditions allow separation of five typical Brassicaceae glucosinolates, including the sulforaphane precursor, glucoraphanin.

Example 3

Consumption of Glucoraphanin as a Function of the Ascorbic Acid Concentration

About 250 mg of broccoli seed extract containing about 12% (w/w) glucoraphanin were subjected to hydrolysis by a fixed concentration of broccoli sprout-derived myrosinase in the presence of variable concentration of ascorbic acid, ranging from 0 to 600 µmoles/Liter. The reaction mixtures were thermostated at 38° C.; aliquots were withdrawn every 15 minutes for 60 minutes, and concentration of glucoraphanin determined chromatographically. The rate of glucoraphanin consumption was interpreted as the rate its conversion to sulforaphane. Graphical representation of glucoraphanin content reduction as a function of increasing ascorbic acid concentration results in a series of linear plots; the slopes of the linear regression lines reflect the rate of glucoraphanin consumption, in µmoles/minute. It is apparent that in the presence of 600 µmoles/Liter concentration of ascorbic acid, the reaction rate increased 13-fold relative to that which proceeded in the absence of modulatory effects of ascorbic acid.

| Time, min | Content of Ascorbic Acid | | | | | | | |
|---|---|---|---|---|---|---|---|---|
| | 0 µM | 50 µM | 125 µM | 250 µM | 250 µM Filtered | 400 µM | 600 µM | |
| 0 | 93.36 | 93.36 | 93.36 | 93.36 | 93.36 | 93.36 | 93.36 | µmoles |
| 15 | 92.24 | 89.20 | 84.52 | 80.95 | 86.31 | 78.32 | 75.02 | GR |
| 30 | 90.71 | 84.24 | 75.92 | 69.06 | 79.44 | 62.78 | 55.66 | |
| 45 | 89.44 | 80.30 | 68.09 | 57.63 | 71.94 | 47.67 | 37.50 | |
| 60 | 87.79 | 76.36 | 59.41 | 45.76 | 65.18 | 33.15 | 22.09 | |
| Slope | −0.09293 | −0.28599 | −0.56217 | −0.79012 | −0.47140 | −1.00714 | −1.20029 | µmol/min |
| Intercept | 93.496 | 93.271 | 93.123 | 93.053 | 93.386 | 93.270 | 92.734 | µmol |

Example 4

Equimolar Conversion of Glucoraphanin to Sulforaphane

A two-part experiment was conducted to further elucidate the role of ascorbic acid in modulating myrosinase activity. All solutions were prepared in 20 mM Tris-buffered saline, at pH 7.5, previously identified as an optimal for myrosinase activity; each sample tube had 100 mg of freeze-dried broccoli powder accurately weighed in as a source of myrosinase. Experiment was conducted at 38° C. for 2 hours, with sample aliquots removed in 30-minute increments, and both glucoraphanin and sulforaphane content assessed by HPLC. A strongly acidic "stop" solution was utilized to instantaneously inhibit further myrosinase activity in the removed aliquots. A control sample contained no ascorbic acid, and the enzymatic conversion proceeded unassisted by a co-factor.

PART 1. In the presence of the fixed concentration of ascorbic acid, 1 mmol/Liter, an increasing amount of broccoli seed extract (about 12% glucoraphanin, w/w) was added, ranging from 250 mg to 500 mg.

PART 2. While keeping the amount of broccoli seed extract fixed at 250 mg, the concentration of ascorbic acid was varied from 0.4 mmol/Liter to 3.8 mmol/Liter.

The table below presents glucoraphanin and sulforaphane expressed in µmoles. It is apparent that within the first 30 minutes in almost all the reaction mixtures, conversion of glucoraphanin to sulforaphane was complete. However, careful examination of the enzymatic conversion occurring in the control sample, without the stimulating effects of ascorbic acid, reveals an equimolar conversion of glucoraphanin to sulforaphane, i.e., the amount of glucoraphanin consumed results in the equivalent amount of sulforaphane produced.

Example 5

Figure 4:
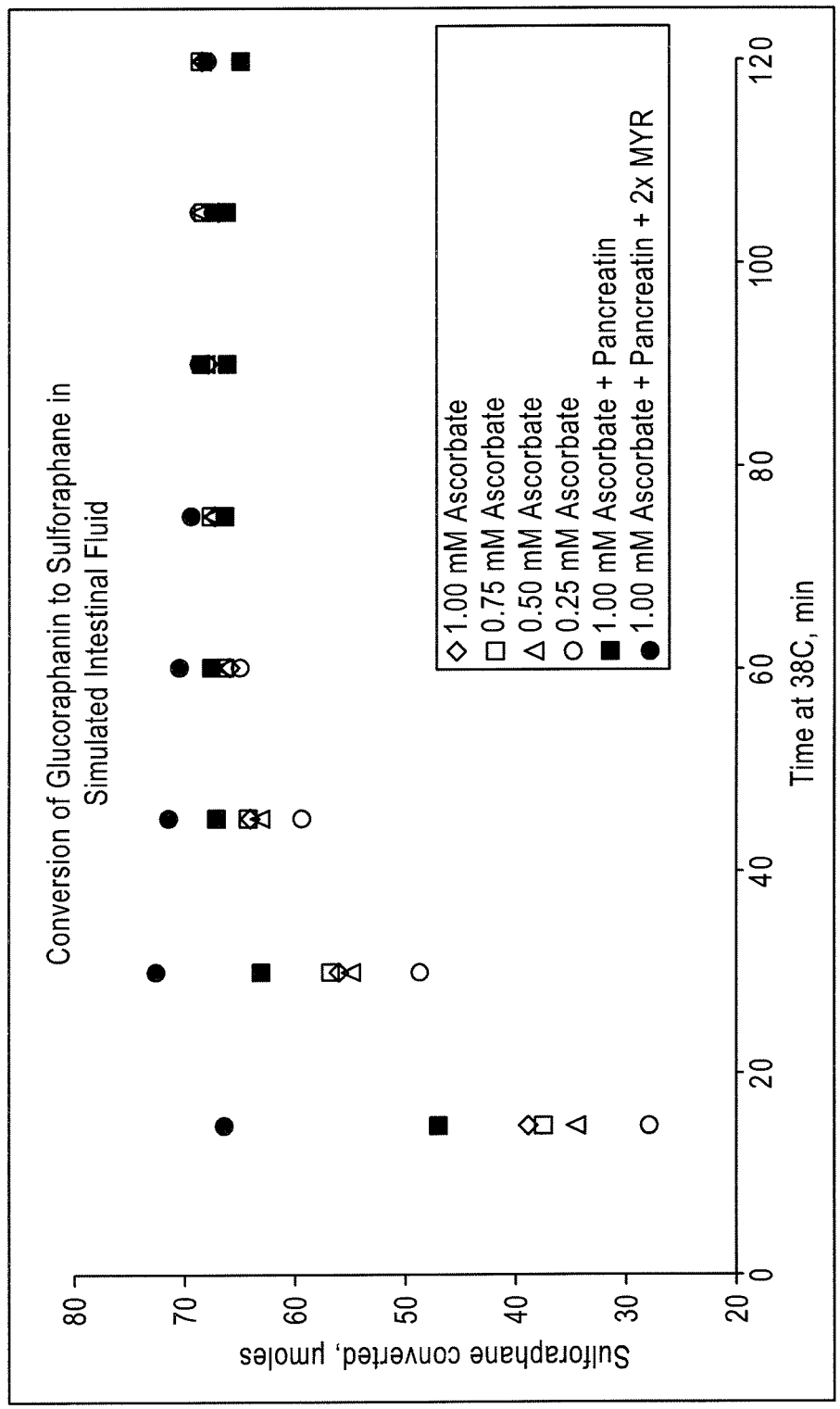
FIG. 4 is a graph showing the conversion of glucoraphanin to sulforaphane in simulated intestinal fluid, as described in Example 5.

Conversion of Glucoraphanin to Sulforaphane in the Presence of Simulated Intestinal Fluid Simulated Intestinal Fluid (SIF) powder, a commercially supplied concentrate closely approximating the human intestinal content in terms of composition, pH and ionic strength, was used. The experiment utilized a USP Dissolution Apparatus 2 (paddles), where into six dissolution vessels 500 mL of Simulated Intestinal Fluid was dispensed, along with 150 mg of freeze-dried broccoli sprout powder as a source of myrosinase. In vessels 1-4, the concentration of ascorbic acid was varied from 0.25 to 1.00 mmol/Liter; in vessel 5, in addition to 1 mmol/Liter ascorbic acid, 3.125 g of pancreatin (8×USP) was suspended; in vessel 6, in addition to 1 mmol/Liter ascorbic acid, and 3.125 g of pancreatin (8×USP), a doubled amount of freeze-dried broccoli sprout powder (300 mg) was added. After vessels were brought to 38° C., 250 mg of glucoraphanin-rich (12%, w/w) broccoli seed extract was added to each, and the resulting suspensions were stirred at 75 RPM for 2 hours. Aliquots were withdrawn every 15 minutes, and assayed for sulforaphane. FIG. 4 shows direct correlation between larger yield of sulforaphane and higher concentrations of ascorbic acid, especially at the earlier stages of the experiment.

Example 6

The following study was conducted to determine the effect of the combination of sulforaphane and a maitake mushroom extract containing 20% b-glucans on gene expression of Nad(P)H:quinone oxidoreductase 1 (NQO-1). NQO-1 encodes a protein that is able to metabolize estrogen quinones, preventing them from forming DNA adducts that cause mutations and ultimately carcinogenesis. An increase

|  | Glucoraphanin, µmoles |  |  |  |  | Sulforaphane, µmoles |  |  |  |  |
|---|---|---|---|---|---|---|---|---|---|---|
| Time, min | 0 | 30 | 60 | 90 | 120 | 0 | 30 | 60 | 90 | 120 |
| GR 250 mg AA 0.0 mM | 58.02 | 48.57 | 37.52 | 26.58 | 15.67 | 3.42 | 12.08 | 22.27 | 33.17 | 42.89 |
| GR 250 mg AA 1.0 mM | 40.07 |  |  |  |  | 21.51 | 61.95 | 60.20 | 60.04 | 58.25 |
| GR 300 mg AA 1.0 mM | 49.31 |  |  |  |  | 24.18 | 74.40 | 73.04 | 72.19 | 70.56 |
| GR 350 mg AA 1.0 mM | 61.41 |  |  |  |  | 25.00 | 84.92 | 84.02 | 83.19 | 80.02 |
| GR 400 mg AA 1.0 mM | 71.35 | 1.56 |  |  |  | 26.71 | 96.60 | 95.38 | 93.39 | 91.16 |
| GR 500 mg AA 1.0 mM | 89.41 | 1.01 |  |  |  | 33.52 | 120.16 | 118.45 | 116.45 | 112.34 |
| GR 250 mg AA 0.4 mM | 45.66 |  |  |  |  | 15.98 | 62.06 | 61.01 | 60.88 | 58.90 |
| GR 250 mg AA 1.0 mM | 35.24 |  |  |  |  | 26.49 | 62.19 | 60.62 | 60.41 | 59.10 |
| GR 250 mg AA 2.0 mM | 24.94 |  |  |  |  | 36.05 | 60.85 | 59.78 | 59.65 | 58.08 |
| GR 250 mg AA 2.9 mM | 22.24 |  |  |  |  | 38.20 | 59.95 | 59.34 | 58.77 | 56.99 |
| GR 250 mg AA 3.8 mM | 21.70 |  |  |  |  | 37.87 | 58.77 | 57.79 | 58.41 | 56.17 |

In the Part 2 of the experiment, the modulatory effect of the increasing concentration of ascorbic acid on the activity of myrosinase was assessed. An initial, apparently linear, increase in myrosinase-promoted conversion of glucoraphanin to sulforaphane is observed to about 2 mmol/L of ascorbic acid concentration, followed subsequently by a considerable leveling off.

Finally, examination of sulforaphane yield of after 30 minutes within the PART 1 of the experiment, reveals that in the presence of 1 mmol/Liter of ascorbic acid, the fixed amount of myrosinase contained in 100 mg of freeze-dried broccoli sprout powder is capable of generating at least 200 µmoles of sulforaphane, in a predictably linear fashion. FIGS. 1, 2, 3, and 4 demonstrate the results of this study.

in NQO-1 expression is favorable for breast, colon, liver, lung, skin and prostate health.

Figure 5:
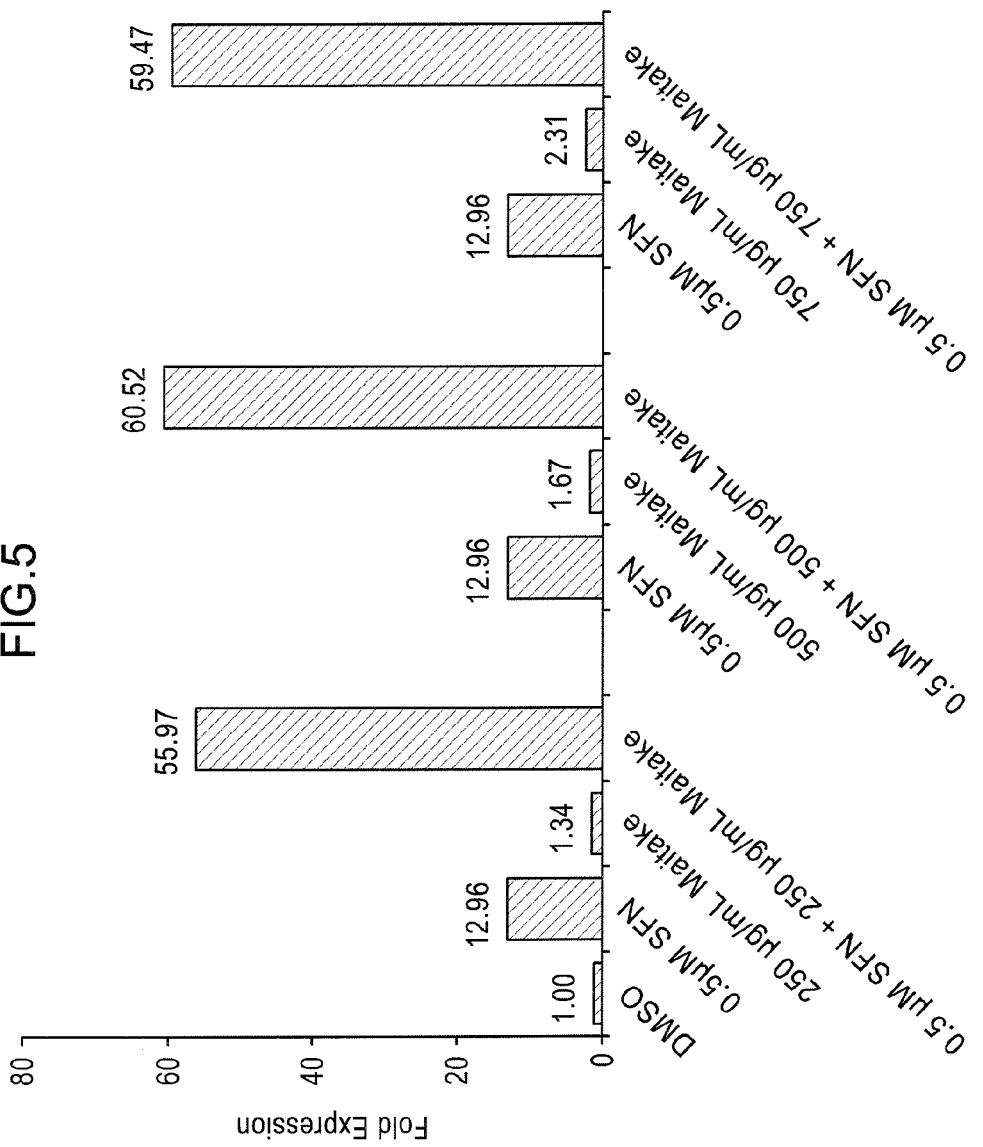
FIG. 5 is a graph showing the results of the experiment described in Example 6.

In the study, the macrophage cell line RAW 264.7 was treated with DMSO (vehicle control), sulforaphane (SFN), maitake mushroom extract having about 20% beta-glucan content (Maitake), or the combination of sulforaphane and maitake mushroom extract, for 24 hours. In particular, the cells were treated with one of the following: (i) DMSO (vehicle control), (ii) 0.5 µM SFN, (iii) 250 µg/mL Maitake, (iv) 500 µg/mL Maitake, (v) 750 µg/mL Maitake, (vi) 0.5 µM SFN and 250 µg/mL Maitake, (vii) 0.5 µM SFN and 500 µg/mL Maitake, and (viii) 0.5 µM SFN and 750 µg/mL Maitake. Gene expression of NQO-1 gene expression was analyzed via quantitative RT-PCR. The results, which are depicted in FIG. 5, show the following:

| Treatment | Fold Increase in NQO-1 gene expression |
| --- | --- |
| DMSO | 1.00 |
| 0.5 µM SFN | 12.96 |
| 250 µg/mL Maitake | 1.34 |
| 0.5 µM SFN + 250 µg/mL Maitake | 55.97 |
| 500 µg/mL Maitake | 1.67 |
| 0.5 µM SFN + 500 µg/mL Maitake | 60.52 |
| 750 µg/mL Maitake | 2.31 |
| 0.5 µM SFN + 750 µg/mL Maitake | 59.47 |

The results demonstrate that the combination of sulforaphane and maitake mushroom extract had a synergistic effect compared to each component alone. This effect was found to be more than merely additive.

Example 7

The following study was conducted to determine the effect of the combination of sulforaphane and a shiitake mushroom extract containing 40% alpha glucans on gene expression of Nad(P)H:quinonequinone oxidoreductase 1 (NQO-1).

Figure 6:
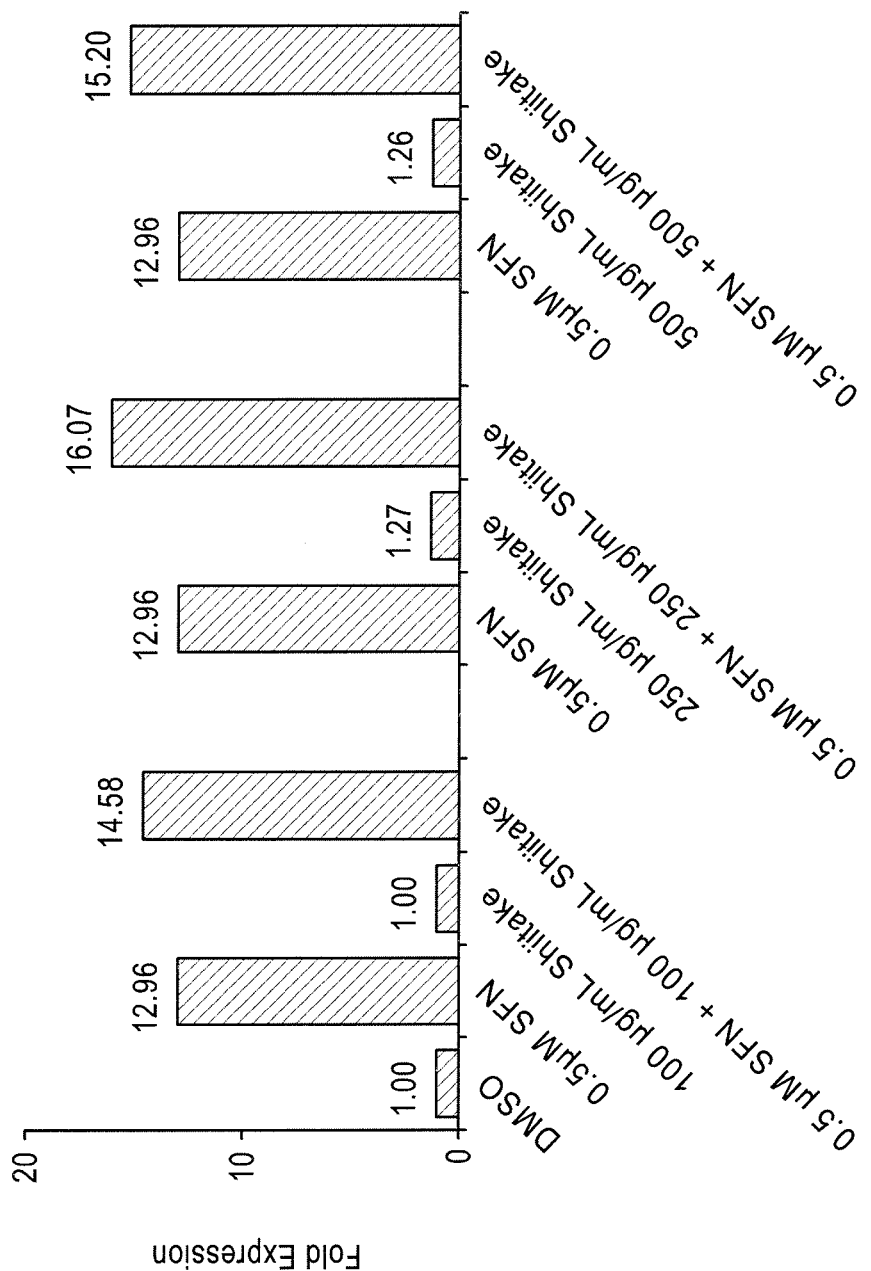
FIG. 6 is a graph showing the results of the experiment described in Example 7.

In the study, the macrophage cell line RAW 264.7 was treated with DMSO (vehicle control), sulforaphane (SFN), shiitake mushroom extract having at least 20% alpha-glucan content (Shiitake), or the combination of sulforaphane and shiitake mushroom extract, for 24 hours. In particular, the cells were treated with one of the following: (i) DMSO (vehicle control), (ii) 0.5 µM SFN, (iii) 100 µg/mL Shiitake, (iv) 250 µg/mL Shiitake, (v) 500 µg/mL Shiitake, (vi) 0.5 µM SFN and 100 µg/mL Shiitake, (vii) 0.5 µM SFN and 250 µg/mL Shiitake, and (viii) 0.5 µM SFN and 500 µg/mL Shiitake. Gene expression of NQO-1 gene expression was analyzed via quantitative RT-PCR. The results, which are depicted in FIG. 6, show the following:

| Treatment | Fold Increase in NQO-1 gene expression |
| --- | --- |
| DMSO | 1.00 |
| 0.5 µM SFN | 12.96 |
| 100 µg/mL Shiitake | 1.00 |
| 0.5 µM SFN + 100 µg/mL Shiitake | 14.58 |
| 250 µg/mL Shiitake | 1.27 |
| 0.5 µM SFN + 250 µg/mL Shiitake | 16.07 |
| 500 µg/mL Shiitake | 1.26 |
| 0.5 µM SFN + 500 µg/mL Shiitake | 15.20 |

The results demonstrate that the combination of sulforaphane and shiitake mushroom extract had a synergistic effect compared to each component alone. This effect was found to be more than merely additive.

Example 8

A subject presents with breast cancer and is suffering from symptoms including damaged breast tissue and breast pain. She is administered a tablet containing glucoraphanin, myrosinase, ascorbic acid, and a maitake mushroom extract. The tablet is an enteric coated formulation which releases the contents in the small intestine. After one month of daily administration of the tablet, the subject experiences modulation of surrogate biomarkers including NQO-1 which correlate with improved in symptoms.

Example 9

A subject presents with breast cancer and is suffering from symptoms including damaged breast tissue and breast pain. She is administered a tablet containing glucoraphanin, myrosinase, ascorbic acid, and a shiitake mushroom extract. The tablet is an enteric coated formulation which releases the contents in the small intestine. After one month of daily administration of the tablet, the subject experiences modulation of surrogate biomarkers including NQO-1 which correlate with improvement in symptoms.

What is claimed:

1. An orally administrable composition comprising a synergistic combination of:
   a sulforaphane precursor;
   a glucosidase enzyme capable of converting the sulforaphane precursor to sulforaphane;
   a cofactor of the enzyme; and
   a maitake mushroom extract or powder.

2. The orally administrable composition of claim 1, wherein the sulforaphane precursor comprises glucoraphanin.

3. The orally administrable composition of claim 1, wherein the enzyme capable of converting the sulforaphane precursor to sulforaphane comprises myrosinase.

4. The orally administrable composition of claim 1, wherein the enzyme cofactor comprises ascorbic acid.

5. The orally administrable composition of claim 1, wherein the composition comprises an enteric-coated dosage form.

6. The orally administrable composition of claim 1, wherein the composition further comprises one or more additional components selected from the group consisting of: quercetin, an aminosugar, a glycosaminoglycan, avocado/soybean unsaponifiables unsaponifiable, a vitamin, coffee fruit, magnesium, silymarin, proanthocyanidins, ursolic acid, curcumin, phytosterols, and phytostanols.

7. The orally administrable composition of claim 1, comprising glucoraphanin, myrosinase, ascorbic acid, and maitake mushroom extract.

8. The orally administrable composition of claim 1, wherein the composition comprises a broccoli extract or powder comprising the sulforaphane precursor.

9. A method of treating, preventing, reducing the occurrence of, decreasing the symptoms associated with, and reducing secondary recurrences of breast cancer, comprising administering to a subject in need thereof a composition comprising a synergistic combination of a sulforaphane precursor; a glucosidase enzyme capable of converting the sulforaphane precursor to sulforaphane; a cofactor of the enzyme; and a maitake mushroom extract or powder.

10. The method of claim 9, wherein the sulforaphane precursor comprises glucoraphanin.

11. The method of claim 9, wherein the enzyme capable of converting the sulforaphane precursor to sulforaphane comprises myrosinase.

12. The method of claim 9, wherein the enzyme cofactor comprises ascorbic acid.

13. The method of claim 9, comprising administration of glucoraphanin, myrosinase, ascorbic acid, and maitake mushroom extract.

14. The method of claim 9, comprising administering an enteric-coated dosage form.

* * * * *